United States Patent
Smith et al.

(10) Patent No.: US 11,673,861 B2
(45) Date of Patent: Jun. 13, 2023

(54) PERFLUORINATED 1-ALKOXYPROPENES, COMPOSITIONS, AND METHODS AND APPARATUSES FOR USING SAME

(71) Applicant: 3M INNOVATIVE PROPERTIES COMPANY, St. Paul, MN (US)

(72) Inventors: Sean M. Smith, Woodbury, MN (US); Michael G. Costello, Afton, MN (US); Klaus Hintzer, Kastl (DE); Markus E. Hirschberg, Mühldorf (DE); William M. Lamanna, Stillwater, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 367 days.

(21) Appl. No.: 15/733,210

(22) PCT Filed: Dec. 12, 2018

(86) PCT No.: PCT/IB2018/059941
§ 371 (c)(1),
(2) Date: Jun. 10, 2020

(87) PCT Pub. No.: WO2019/116260
PCT Pub. Date: Jun. 20, 2019

(65) Prior Publication Data
US 2020/0386488 A1  Dec. 10, 2020

Related U.S. Application Data

(60) Provisional application No. 62/598,278, filed on Dec. 13, 2017.

(51) Int. Cl.
C07D 207/08 (2006.01)
C07D 241/04 (2006.01)
(Continued)

(52) U.S. Cl.
CPC ............ *C07D 207/08* (2013.01); *C07C 43/17* (2013.01); *C07C 217/26* (2013.01);
(Continued)

(58) Field of Classification Search
CPC ................ C07D 207/08; C07D 241/04; C07D 295/088; C07D 207/04; C07D 295/067;
(Continued)

(56) References Cited

U.S. PATENT DOCUMENTS

| 3,184,533 A | 5/1965 | Eiseman, Jr. |
| 3,752,840 A | 8/1973 | Oxenrider |

(Continued)

FOREIGN PATENT DOCUMENTS

| CN | 102834481 A | * 12/2012 | ......... B23K 35/0244 |
| CN | 101448806 B | * 1/2013 | ........... C07D 307/20 |

(Continued)

OTHER PUBLICATIONS

Abe, "A New Route to Perfluorovinylamines by the Pyrolytic Reaction of an Alkali Metal Salt of Perfluoro (2-dialkylamino-propionic acids)", Chemistry Letters, 1988, vol. 17, No. 11, pp. 1887-1890.

(Continued)

*Primary Examiner* — Emmanuel E Duke
(74) *Attorney, Agent, or Firm* — Jeffrey M. Olofson

(57) ABSTRACT

A perfluorinated 1-alkoxypropene represented by general Formula (I), compositions that include such compounds, and methods and systems that include such compositions are provided, wherein Formula (I) is represented by: $R_fO-CF=CFCF_3$ wherein $R_f$ is a linear, branched, or cyclic perfluoroalkyl group having 2 to 10 carbon atoms and optionally further including 1 to 3 nitrogen and/or 1 to 4 oxygen catenary heteroatoms.

20 Claims, 1 Drawing Sheet

(51) Int. Cl.
  *C07D 295/088* (2006.01)
  *C09K 5/04* (2006.01)
  *C07C 217/26* (2006.01)
  *C07C 43/17* (2006.01)
  *H05K 7/20* (2006.01)
  *F28D 15/02* (2006.01)
  *F28F 23/00* (2006.01)

(52) U.S. Cl.
  CPC ........ *C07D 241/04* (2013.01); *C07D 295/088* (2013.01); *C09K 5/045* (2013.01); *H05K 7/20818* (2013.01); *F28D 15/025* (2013.01); *F28F 23/00* (2013.01)

(58) Field of Classification Search
  CPC ........ C07C 43/17; C07C 217/26; C09K 5/045; C09K 5/10; H05K 7/20818; F28D 15/025; F28D 15/02; F28F 23/00
  See application file for complete search history.

(56) References Cited

U.S. PATENT DOCUMENTS

| | | | |
|---|---|---|---|
| 4,288,651 A | 9/1981 | Wootton | |
| 4,741,744 A | 5/1988 | Wu | |
| 4,782,148 A | 11/1988 | Abe | |
| 4,899,249 A | 2/1990 | Reilly | |
| 4,985,556 A | 1/1991 | Abe | |
| 5,962,390 A | 10/1999 | Flynn | |
| 7,385,089 B2 * | 6/2008 | Costello | C08G 65/007 568/675 |
| 7,736,537 B1 | 6/2010 | Zastrow | |
| 8,418,530 B1 | 4/2013 | Scaringe | |
| 9,837,801 B2 | 12/2017 | Kieffel | |
| 9,899,125 B2 | 2/2018 | Kieffel | |
| 10,643,764 B2 | 5/2020 | Biquez | |
| 2009/0048424 A1 | 2/2009 | Watakabe | |
| 2011/0076572 A1 | 3/2011 | Amine | |
| 2015/0083979 A1 | 3/2015 | Costello | |
| 2016/0312096 A1 * | 10/2016 | Bulinski | A62D 1/0057 |
| 2018/0040391 A1 | 2/2018 | Kieffel | |
| 2018/0358148 A1 | 12/2018 | Kieffel | |
| 2019/0156968 A1 | 5/2019 | Gautschi | |

FOREIGN PATENT DOCUMENTS

| | | | | |
|---|---|---|---|---|
| EP | 0694532 A1 * | 5/2000 | | |
| EP | 1325949 | 7/2003 | | |
| EP | 2552638 B1 * | 4/2015 | ......... | B23K 35/0244 |
| GB | 1242180 | 8/1971 | | |
| GB | 2070012 | 9/1981 | | |
| JP | S56-25133 | 3/1981 | | |
| JP | S56-55336 | 5/1981 | | |
| JP | S64-70445 | 3/1989 | | |
| JP | H05-325970 | 12/1993 | | |
| JP | H08-291299 | 11/1996 | | |
| JP | 2001342458 | 12/2001 | | |
| JP | 2001342458 A * | 12/2001 | ......... | F28D 15/0266 |
| JP | 2002-187863 | 7/2002 | | |
| JP | 2013523639 A * | 6/2013 | ............... | C09K 5/10 |
| KR | 20130018267 A * | 2/2013 | | |
| KR | 20130018268 A * | 2/2013 | ............... | C09K 5/10 |
| TW | 201546028 A * | 12/2015 | ........... | A62D 1/0057 |
| WO | WO 1999-037598 | 7/1999 | | |
| WO | WO 2000-015588 | 3/2000 | | |
| WO | WO 2000-070289 | 11/2000 | | |
| WO | WO 2002-040102 | 5/2002 | | |
| WO | WO-2007030314 A2 * | 3/2007 | ......... | C07C 43/126 |
| WO | 2008006866 | 1/2008 | | |
| WO | WO-2008006866 A1 * | 1/2008 | ............... | C09K 3/30 |
| WO | WO 2009-141053 | 11/2009 | | |
| WO | WO 2012-102915 | 8/2012 | | |
| WO | WO 2013-151741 | 10/2013 | | |
| WO | WO 2014-037566 | 3/2014 | | |
| WO | WO 2014-110329 | 7/2014 | | |
| WO | WO 2015-013155 | 1/2015 | | |
| WO | WO 2015-040069 | 3/2015 | | |
| WO | WO 2015-071303 | 5/2015 | | |
| WO | WO 2015-097143 | 7/2015 | | |
| WO | WO 2016-048808 | 3/2016 | | |
| WO | WO 2016-094113 | 6/2016 | | |
| WO | WO 2016-096129 | 6/2016 | | |
| WO | WO 2016-109203 | 7/2016 | | |
| WO | WO 2016-116637 | 7/2016 | | |
| WO | WO 2016-128571 | 8/2016 | | |
| WO | WO 2016-198390 | 12/2016 | | |
| WO | WO 2017-093259 | 6/2017 | | |
| WO | WO 2017-108141 | 6/2017 | | |
| WO | WO 2017-114862 | 7/2017 | | |
| WO | WO 2017-125536 | 7/2017 | | |
| WO | WO 2017-195070 | 11/2017 | | |
| WO | WO 2018-039096 | 3/2018 | | |
| WO | WO 2018-222384 | 12/2018 | | |
| WO | WO 2018-224908 | 12/2018 | | |
| WO | WO 2019-082053 | 5/2019 | | |
| WO | WO 2019-116262 | 6/2019 | | |
| WO | WO 2019-116264 | 6/2019 | | |

OTHER PUBLICATIONS

Abe, "An Alternative New Route to Perfluorovinylamines. Pyrolysis of an Alkali Metal Salt of Perfluoro (3-dialkylamino-propionic acids)", Chemistry Letters, 1989, vol. 18, No. 5, pp. 905-908.

Abe, "The Electrochemical Fluorination of Nitrogen-Containing Carboxylic Acids. Fluorination of Dimethylamino-Substituted Carboxylic Acid Derivatives", Journal of Fluorine Chemistry, 1990, vol. 48, pp. 257-279.

Abe, "The Electrochemical Fluorination of Nitrogen-Containing Carboxylic Acids. Fluorination of Methyl Esters of Cyclic Amino-Group Substituted Carboxylic Acids", Journal of Fluorine Chemistry, 1990, vol. 50, pp. 173-196.

Andersen, "Atmospheric Chemistry of (CF3)2CF-C° N: A Replacement Compound for the Most Potent Industrial Greenhouse Gas, SF6", Environmental Science & Technology, 2017, Vo. 51 No. 3, pp. 1321-1329.

Barlow, "Heterocyclic Polyfluoro-Compounds. Part 30. Perfluoroalkylation of trifluoro-1,2,4-triazine", Journal of the Chemical Society, Perkin Transactions 1: Organic and Bio-Organic Chemistry, 1980, pp. 2254-2257.

Barnes, "Photochemistry of halocarbon compounds. Part 4. Photochemical conversions of some fluorinated aza- and Diazacyclohexadienes", Journal of the Chemical Society, Perkin Transactions 1: Organic and Bio-Organic Chemistry, 1981, pp. 3289-3291.

Chambers, "Photochemical conversions of some fluorinated aza- and diazacyclohexadienes", Journal of the Chemical Society, Chemical Communications, 1978, No. 7, pp. 305-306.

Chambers, "Photochemistry of halocarbon compounds. Part 5. Photolysis of fluorinated 1,2,3-triazine derivatives", Journal of the Chemical Society, Perkin Transactions 1: Organic and Bio-Organic Chemistry,1990, No. 4, pp. 975-981.

Chambers, "Photochemistry of halocarbon compounds. Part 6. Direct Observation of fluorinated azetes", Journal of the Chemical Society, Perkin Transactions 1: Organic and Bio-Organic Chemistry, 1990, No. 4, pp. 983-987.

Chambers, "Possible generation of a fluorinated azacyclobutadiene", Journal of the Chemical Society, Chemical Communications, 1976, No. 24, pp. 1005-1006.

Cheburkov, "Perfluoroalcohols", Journal of Fluorine Chemistry, Dec. 2002, vol. 118, No. 1-2, pp. 123-126.

Chepik, "Electrophilic Alkenylation of Fluoroolefins with Perfluoro(2-alkoxypropenes)", Bulletin of the Academy of Sciences of the USSR, Division of chemical science, Aug. 1991, vol. 40, pp. 1712-1714 (Translated from Izvestiya Akademii Nauk SSSR Seriya Khimicheskaya, No. 8, pp. 1926-1928).

Cherstov, "Sulfotrioxidation of perfluoroisopropyl alkenyl ethers", Bulletin of the Academy of Sciences of the USSR, Division of

(56) References Cited

OTHER PUBLICATIONS chemical science, Dec. 1982, vol. 31, pp. 2472-2473 (Translated from Izvestiya Akademii Nauk SSSR Seriya Khimicheskaya, No. 12, pp. 2796-2798).
Ellis, "Cleaning and Contamination of Electronics Components and Assemblies", Electrochemical Publications Limited, 1986, pp. 182-194.
Galimberti, "New catalytic alkylation of in situ generated perfluoro-alkyloxy-anions and perfluoro-carbanions", Journal of Fluorine Chemistry, Dec. 2005, vol. 126, No. 11-12, pp. 1578-1586.
Jelier, "A Convenient Route to Tetraalkylammonium Perfluoroalkoxides from Hydrofluoroethers", Angewandte Chemie International Edition, Mar. 2015, vol. 54, No. 10, pp. 2945-2949.
McLinden, "A Thermodynamic Analysis of Refrigerants: Possibilities and Tradeoffs for Low-GWP Refrigerants", International Journal of Refrigeration, Feb. 2014, vol. 38, pp. 80-92.
OECD Test No. 436: "Acute Inhalation Toxicity-Acute Toxic Class Method", OECD Guideline for The Testing of Chemicals, Sep. 2009, 27 pages.
OPPTS 870.1100: "Acute Oral Toxicity" U.S. EPA Health Effects Test Guidelines, Dec. 2002, 37 pages.
Pinnock, "Radiative forcing of climate by hydrochlorofluorocarbons and hydrofluorocarbons", Journal of Geophysical Research: Atmospheres, Nov. 1995, vol. 100, No. D11, pp. 23227-23238.
Wlassics, "Perfluoro Allyl Fluorosulfate (FAFS): A Versatile Building Block for New Fluoroallylic Compounds", Molecules, Dec. 2011, vol. 16, No. 8, pp. 6512-6540.
International Search Report for PCT International Application No. PCT-IB2018-059941, dated Mar. 25, 2019, 5pages.
International Search Report for PCT International Application No. PCT-IB2018-059943, dated Mar. 27, 2019, 5pages.
International Search Report for PCT International Application No. PCT-IB2018-059946, dated Mar. 15, 2019, 4pages.

* cited by examiner

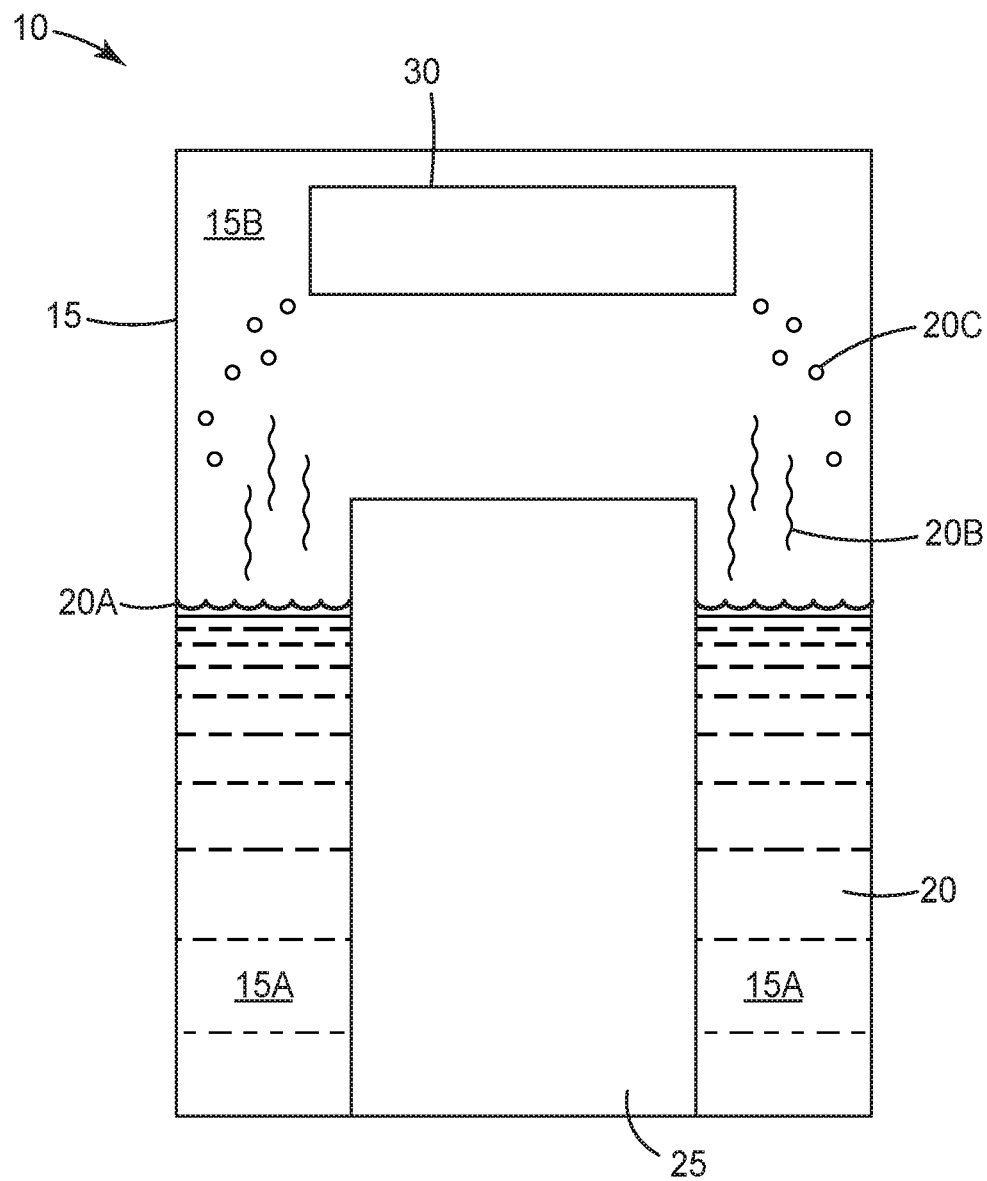

PERFLUORINATED 1-ALKOXYPROPENES, COMPOSITIONS, AND METHODS AND APPARATUSES FOR USING SAME

CROSS REFERENCE TO RELATED APPLICATIONS

This application is a national stage filing under 35 U.S.C. 371 of PCT/IB2018/059941, filed Dec. 12, 2018, which claims the benefit of U.S. Provisional Application No. 62/598,278, filed Dec. 13, 2017, the disclosure of which is incorporated by reference in its/their entirety herein.

BACKGROUND

There continues to be a need for inert fluorinated fluids that have low global warming potential while providing high thermal stability, low toxicity, nonflammability, good solvency, and a wide operating temperature range to meet the requirements of various applications. Those applications particularly include, but are not restricted to, heat transfer fluids.

SUMMARY

The present disclosure provides perfluorinated 1-alkoxypropene compounds, compositions including such compounds, and apparatuses and methods that include the use of such compounds and compositions.

The perfluorinated 1-alkoxypropene is represented by the following general Formula (I):

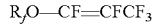
$$R_fO-CF=CFCF_3 \qquad \qquad I$$

wherein $R_f$ is a linear, branched, or cyclic perfluoroalkyl group having 2 to 10 carbon atoms and optionally further including 1 to 3 nitrogen and/or 1 to 4 oxygen catenary heteroatoms. In certain embodiments, $R_f$ is not a branched perfluoroalkyl group having 3 carbon atoms and no heteroatoms.

In some embodiments, an apparatus for heat transfer is provided that includes: a device; and a mechanism for transferring heat to or from the device, the mechanism including a heat transfer fluid that includes the perfluorinated 1-alkoxypropene of Formula I. In some embodiments, the apparatus for heat transfer includes an immersion cooling system.

In some embodiments, a method of transferring heat is provided. The method includes providing a device, and transferring heat to or from the device using a heat transfer fluid that includes the perfluorinated 1-alkoxypropene of Formula I.

Herein, "device" refers to an object or contrivance which is heated, cooled, or maintained at a predetermined temperature.

The term "mechanism" refers to a system of parts or a mechanical appliance including a heat transfer fluid.

The term "alkyl" refers to a monovalent group that is a radical of an alkane, which is a saturated hydrocarbon. The alkyl group can be linear, branched, cyclic, or combinations thereof, "perfluoro-" (for example, in reference to a group or moiety, such as in the case of "perfluoroalkyl") and "perfluorinated" mean a group or compound completely fluorinated such that all hydrogen atoms in the C—H bonds have been replaced by C—F bonds; and a chemical structure that depicts the letter "F" in the center of a ring indicates that all unmarked bonds of the ring are fluorine atoms.

Herein, the term "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements. Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof).

The words "preferred" and "preferably" refer to embodiments of the disclosure that may afford certain benefits, under certain circumstances. However, other claims may also be preferred, under the same or other circumstances. Furthermore, the recitation of one or more preferred claims does not imply that other claims are not useful and is not intended to exclude other claims from the scope of the disclosure.

In this application, terms such as "a," "an," and "the" are not intended to refer to only a singular entity but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also, herein, all numbers are assumed to be modified by the term "about" and in certain embodiments, preferably, by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also, herein, the recitations of numerical ranges by endpoints include all numbers subsumed within that range as well as the endpoints (e.g., 1 to 5 includes 1, 1.5, 2, 2.75, 3, 3.80, 4, 5, etc.).

As used herein, the term "room temperature" refers to a temperature of 20° C. to 25° C. or 22° C. to 25° C.

The term "in the range" or "within a range" (and similar statements) includes the endpoints of the stated range.

Groupings of alternative elements or embodiments disclosed herein are not to be construed as limitations. Each group member may be referred to and claimed individually or in any combination with other members of the group or other elements found therein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Reference throughout this specification to "one embodiment," "an embodiment," "certain embodiments," or "some embodiments," etc., means that a particular feature, configuration, composition, or characteristic described in connection with the embodiment is included in at least one embodiment of the invention. Thus, the appearances of such phrases in various places throughout this specification are not necessarily referring to the same embodiment of the invention. Furthermore, the particular features, configurations, compositions, or characteristics may be combined in any suitable manner in one or more embodiments.

The above summary of the present disclosure is not intended to describe each disclosed embodiment or every implementation of the present invention. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list. Thus, the scope of the present disclosure should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired. Although various theories and possible mechanisms may have been discussed herein, in no event should such discussions serve to limit the claimable subject matter.

BRIEF DESCRIPTION OF THE FIGURE

FIG. 1 is a two-phase immersion cooling system that includes a heat transfer fluid that includes a perfluorinated 1-alkoxypropene compound as disclosed herein.

DETAILED DESCRIPTION

The present disclosure provides perfluorinated 1-alkoxypropene compounds, compositions (i.e., fluids) including such compounds, and apparatuses and methods that include the use of such compounds and compositions.

In some embodiments, the present disclosure is directed to a perfluorinated 1-alkoxypropene represented by the following general Formula (I):

$$R_fO-CF=CFCF_3 \qquad I$$

wherein $R_f$ is a linear, branched, or cyclic perfluoroalkyl group having 2 to 10 carbon atoms and optionally further including 1 to 3 nitrogen and/or 1 to 4 oxygen catenary heteroatoms. Such heteroatoms may be included in a N- and/or O-containing 5- or 6-membered perfluorinated ring (preferably a 6-membered perfluorinated ring), which may be a monovalent ring (at the terminus of an alkyl group) or a divalent ring (within the chain of an alkyl group).

Some embodiments of Formula (I) include a proviso that $R_f$ is not a branched perfluoroalkyl group having 3 carbon atoms and no heteroatoms. Some embodiments of Formula (I) include a proviso that $R_f$ is not a branched perfluoroalkyl group having no heteroatoms.

In some embodiments of the perfluorinated 1-alkoxypropenes of Formula (I), $R_f$ is a linear, branched, or cyclic perfluoroalkyl group having 3 to 10 carbon atoms. In some embodiments of the perfluorinated 1-alkoxypropenes of Formula (I), $R_f$ is a linear, branched, or cyclic perfluoroalkyl group having 2 to 6 carbon atoms.

In some embodiments of the perfluorinated 1-alkoxypropenes of Formula (I), $R_f$ is a linear or branched perfluoroalkyl group. In some embodiments, a mixture of perfluorinated 1-alkoxypropene compounds of Formula (I) is provided (e.g., as in a heat transfer fluid), wherein at least a portion of which includes linear $R_f$ groups and at least a portion of which includes branched $R_f$ groups.

In some embodiments of the perfluorinated 1-alkoxypropenes of Formula (I), $R_f$ is a linear perfluoroalkyl group. In some embodiments, $R_f$ is a linear perfluoroalkyl group having 2 to 6 carbon atoms and optionally further including 1 to 3 nitrogen and/or 1 to 4 oxygen catenary heteroatoms.

In some embodiments of the perfluorinated 1-alkoxypropenes of Formula (I), $R_f$ includes 1 to 3 nitrogen and/or 1 to 4 oxygen catenary heteroatoms. In some embodiments of the perfluorinated 1-alkoxypropenes of Formula (I), $R_f$ includes a N- and/or O-containing 5- or 6-membered perfluorinated ring. In some embodiments of the perfluorinated 1-alkoxypropenes of Formula (I), $R_f$ includes an oxygen atom. In some embodiments of the perfluorinated 1-alkoxypropenes of Formula (I), $R_f$ is a perfluoroalkyl group that does not include oxygen or nitrogen atoms.

In some embodiments of the perfluorinated 1-alkoxypropenes of Formula (I), $R_f$ is a perfluoroalkyl group having the formula $-(CF_2)_nCF_3$ or $-(CF_2)_nOCF_3$, wherein n=1 to 6.

In some embodiments of the perfluorinated 1-alkoxypropenes of Formula (I), the N- and/or O-containing perfluorinated ring is selected from the group of:

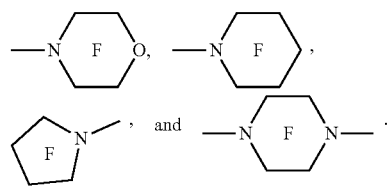

In some embodiments, the perfluorinated 1-alkoxypropene of Formula (I) is selected from one of the following:
$CF_3CF_2O-CF=CF-CF_3$ $CF_3(CF_2)_2O-CF=CF-CF_3$ $CF_3(CF_2)_3O-CF=CF-CF_3$ $CF_3(CF_2)_4O-CF=CF-CF_3$ $CF_3(CF_2)_5O-CF=CF-CF_3$ $CF_3(CF_2)_6O-CF=CF-CF_3$ $CF_3(CF_2)_7O-CF=CF-CF_3$ $CF_3O(CF_2)_3O-CF=CF-CF_3$ $CF_3OCF_2OCF_2CF_2O-CF=CF-CF_3$ $CF_3OCF_2OCF_2OCF_2CF_2O-CF=CF-CF_3$

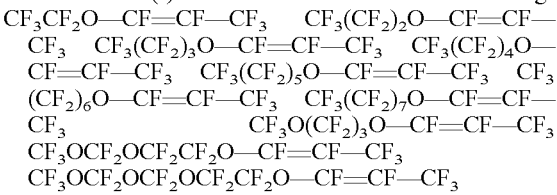

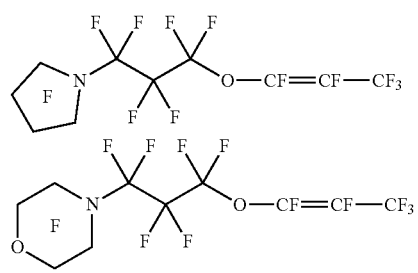

-continued

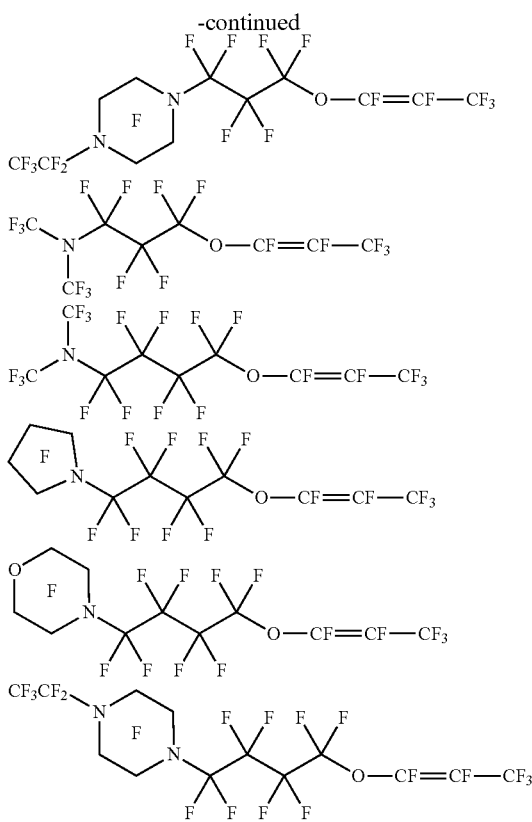

In some embodiments, the perfluorinated 1-alkoxypropene of Formula (I) is $CF_3$—O—$(CF_2)_3$—O—CF=CF—$CF_3$.

In some embodiments, the perfluorinated 1-alkoxypropene of Formula (I) is $CF_3$—$CF_2$—O—CF=CF—$CF_3$.

In some embodiments, the perfluorinated 1-alkoxypropene of Formula (I) is $CF_3$—$CF_2$—$CF_2$—O—CF=CF—$CF_3$.

In some embodiments, the perfluorinated 1-alkoxypropenes of Formula (I) of the present disclosure may be in a cis configuration or a trans configuration. In some embodiments, a mixture of perfluorinated 1-alkoxypropene compounds of Formula (I) is provided (e.g., as in a heat transfer fluid), wherein at least a portion of which are in the cis configuration and at least a portion of which are in the trans configuration.

The perfluorinated 1-alkoxypropene compounds of Formula (I) possess good environmental properties, good performance attributes, nonflammability, chemical inertness, high thermal stability, good solvency, etc. In some embodiments, the perfluorinated 1-alkoxypropene compounds of Formula (I) of the present disclosure may possess the required stability as well as the necessary short atmospheric lifetime and hence low global warming potential to make them viable environmentally friendly candidates for high temperature heat transfer applications, for example, for the electronics industry. For example, the perfluorinated 1-alkoxypropene compounds of Formula (I) may be chemically inert (i.e., they do not easily react with base, acid, water, etc.), and may have high boiling points (up to 300° C.), low freezing points (they may be liquid at −40° C. or lower), low viscosity, high thermal stability, good thermal conductivity, adequate solvency in a range of potentially useful solvents, and low toxicity.

The useful liquid range of a perfluorinated 1-alkoxypropene compound of the present disclosure is between its pour point and its boiling point. A pour point is the lowest temperature at which the compound is still able to be poured. The pour point can be determined, for example, by ASTM D97-16 "Standard Test Method for Pour Point of Petroleum Products." In one embodiment, the compounds of the present disclosure have a pour point of less than −100° C., less than −120° C., less than −130° C., or less than −140° C. Pour Point can be measured by placing a sealed glass vial containing 3 mL of the fluid into a refrigerated bath, adjusting temperature incrementally and checking for pouring. Pouring is defined as visible movement of the material during a five second count. This criterion is specified in ASTM D97-16.

In some embodiments, the perfluorinated 1-alkoxypropene compounds are expected to provide low acute toxicity based on 4-hour acute inhalation or oral toxicity studies in rats following U.S. EPA "Health Effects Test Guidelines OPPTS 870.1100 Acute Oral Toxicity" and/or OECD Test No. 436 "Acute Inhalation Toxicity-Acute Toxic Class Method." For example, a compound of the present disclosure has a single dose oral median lethal dose (LD 50) in male and female Sprague-Dawley rats of at least 5,000 parts per million (ppm), at least 10,000 ppm, at least 15,000 ppm, or at least 20,000 ppm.

Furthermore, in some embodiments, the perfluorinated 1-alkoxypropene compounds of the present disclosure may have a low environmental impact. In this regard, the perfluorinated 1-alkoxypropenes may have a global warming potential (GWP) of less than 150, less than 120, less than 100, less than 80, less than 50, less than 25, or less than 10. As used herein, GWP is a relative measure of the warming potential of a compound based on the structure of the compound. The GWP of a compound, as defined by the Intergovernmental Panel on Climate Change (IPCC) in 1990 and updated in 2007, is calculated as the warming due to the release of 1 kilogram of a compound relative to the warming due to the release of 1 kilogram of $CO_2$ over a specified integration time horizon (ITH).

$$GWP_i(t') = \frac{\int_0^{ITH} a_i[C(t)]dt}{\int_0^{ITH} a_{CO_2}[C_{CO_2}(t)]dt} = \frac{\int_0^{ITH} a_i C_{oi} e^{-t/\tau_i} dt}{\int_0^{ITH} a_{CO_2}[C_{CO_2}(t)]dt}$$

In this equation $a_i$ is the radiative forcing per unit mass increase of a compound in the atmosphere (the change in the flux of radiation through the atmosphere due to the IR absorbance of that compound), C is the atmospheric concentration of a compound, τ is the atmospheric lifetime of a compound, t is time, and i is the compound of interest. The commonly accepted ITH is 100 years representing a compromise between short-term effects (20 years) and longer-term effects (500 years or longer). The concentration of an organic compound, i, in the atmosphere is assumed to follow pseudo first order kinetics (i.e., exponential decay). The concentration of $CO_2$ over that same time interval incorporates a more complex model for the exchange and removal of $CO_2$ from the atmosphere (the Bern carbon cycle model).

In some embodiments, the perfluorinated 1-alkoxypropenes of the present disclosure are nonflammable. Nonflammability can be assessed by using standard methods such as ASTM D-3278-96 e-1, D56-05 "Standard Test Method for Flash Point of Liquids by Small Scale Closed-Cup Apparatus." In one embodiment, the compound of the present disclosure is nonflammable based on closed-cup flashpoint testing following ASTM D-3278-96 e-1.

In some embodiments, the perfluorinated 1-alkoxypropenes of the present disclosure have a dielectric constant of less than 2.5, less than 2.4, less than 2.3, less than 2.2, less than 2.1, less than 2.0, or less than 1.9, as measured in accordance with ASTM D150-11 at room temperature and 1 KHz. Such compounds have a dielectric constant such that high frequency electronic components and connectors can be submerged therein without significant loss of signal integrity.

The perfluorinated 1-alkoxypropene compounds of Formula (I) can be prepared from reaction of a Lewis Acid with a perfluoroalkyl ether compound represented by the following general Formula (II):

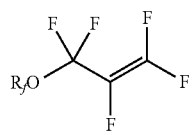

II wherein $R_f$ is as described for Formula (I).

Examples of perfluoroalkyl compounds of Formula (II) include:

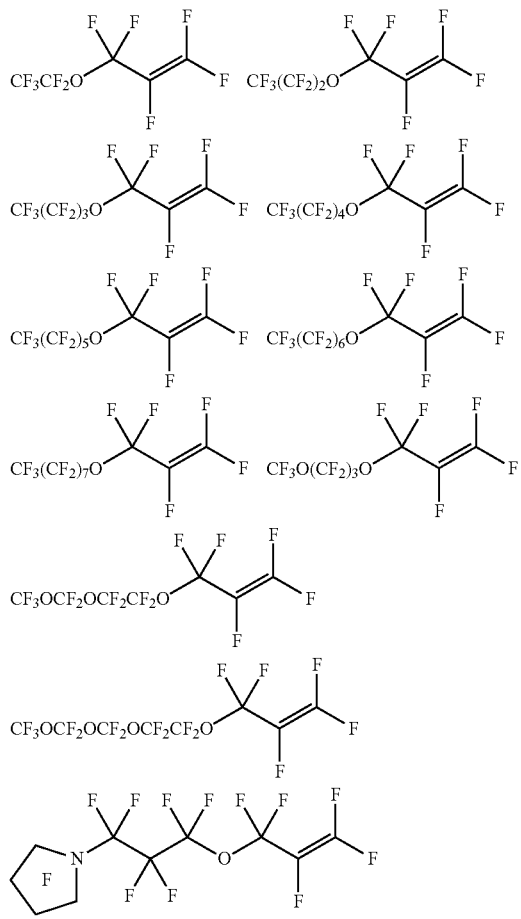

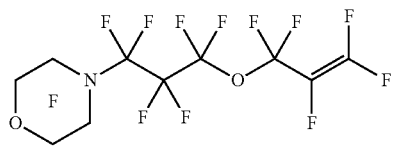

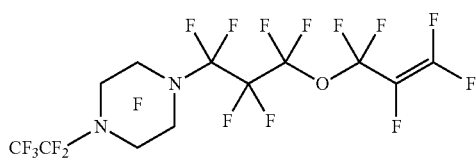

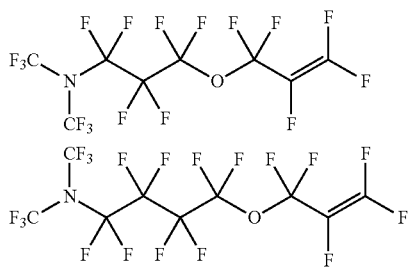

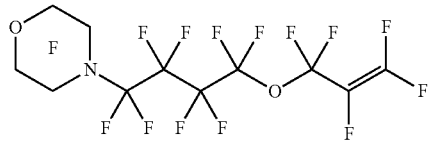

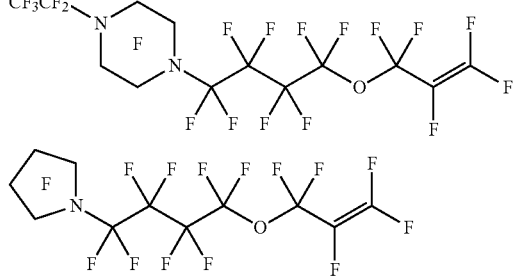

Examples of Lewis Acids include $TiF_4$, $ZrF_4$, $NbF_5$, $TaF_5$, $BF_3$, $SbF_5$, ACF (aluminum chlorofluoride), $SbCl_2F_3$, $SbCl_4F$, $HSbF_6$, $SbCl_5$, $AlCl_3$, and mixtures thereof.

Such method results in a perfluorinated 1-alkoxypropene compound represented by Formula (I) contaminated with less than 15 wt-% of a perfluoroketone of the following general Formula (III) (without purification of the perfluorinated 1-alkoxypropene of Formula (I)):

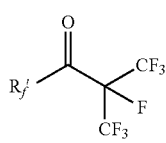

III wherein $R_f$ has one fewer carbon than $R_f$.

This reaction can be represented by the following Scheme 1:

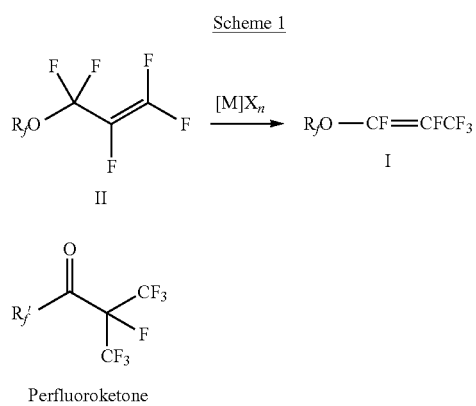

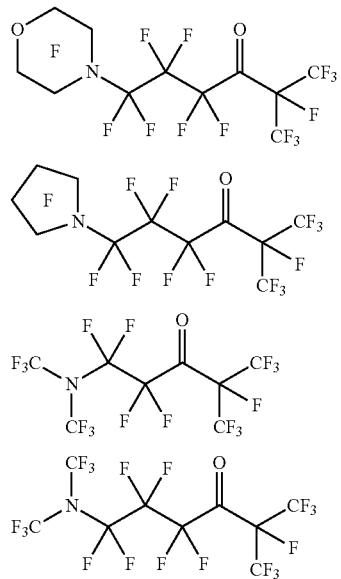

Examples of perfluoroketones of Formula (III) include:

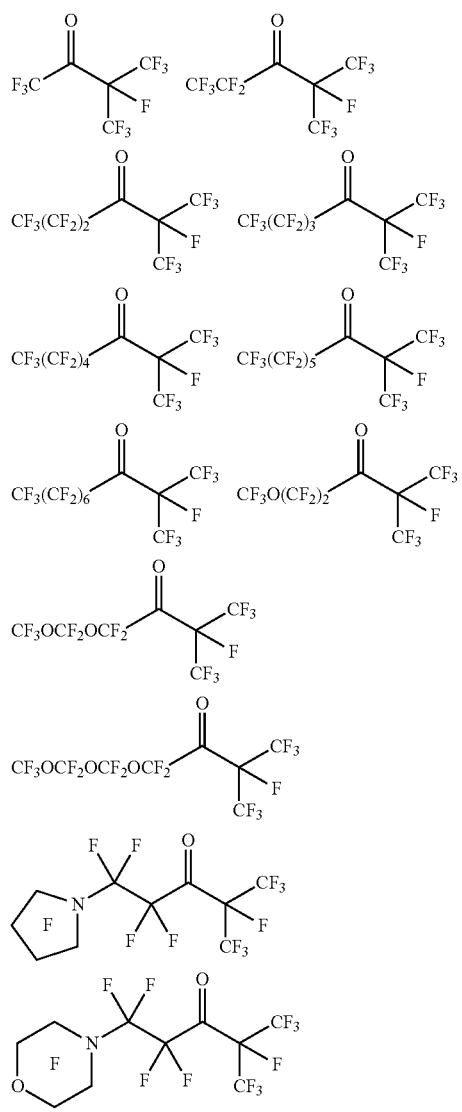

The perfluoroalkyl ethers of Formula (II) and can be prepared from their respective perfluorinated acid fluorides in combination with perfluoroalkyl fluorosulfate (FAFS) and sub-stoichiometric amounts of a metal fluoride (e.g., KF or CsF) typically at less than room temperature as described, for example, in *Molecules* 2011, 16, 6512-6540.

Examples of perfluorinated acid fluorides include:

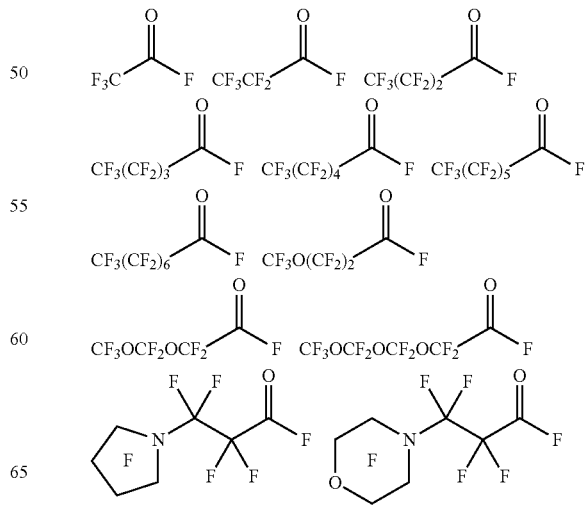

-continued

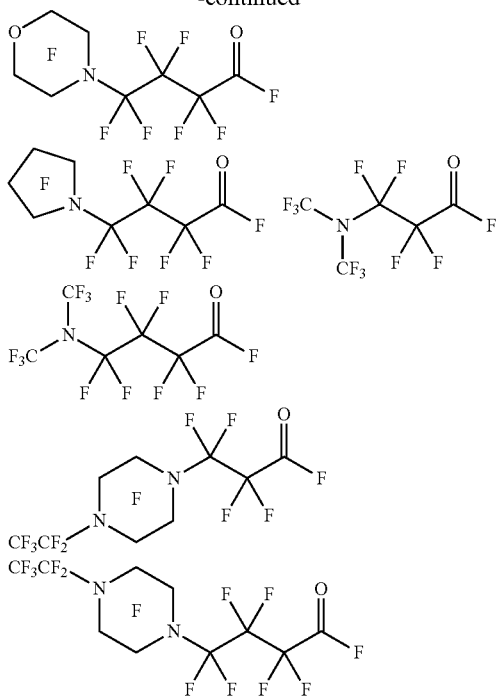

Compositions (i.e., fluids) that include perfluorinated 1-alkoxypropene compounds of Formula (I) may be used for a variety of applications. For example, the perfluorinated 1-alkoxypropenes are believed to possess the required stability as well as the necessary short atmospheric lifetime and hence low global warming potential to make them viable environmentally friendly candidates for high temperature heat transfer applications.

In certain embodiments, a perfluorinated 1-alkoxypropene compound is in purified form.

Minor amounts of optional components can also be added to the compositions to impart particular desired properties for particular uses. Useful components can include conventional additives such as, for example, surfactants, coloring agents, stabilizers, anti-oxidants, flame retardants, and the like, and mixtures thereof.

The properties (e.g., GWP, dielectric constant) described herein for the compounds also apply to the compositions (i.e., fluids) in which they are incorporated.

Heat Transfer Compositions and Methods

Presently, various fluids are used for heat transfer. The suitability of the heat transfer fluid depends upon the application process. For example, in some electronic applications, a heat-transfer fluid is inert, has a high dielectric strength, low toxicity, good environmental properties, and good heat transfer properties over a wide temperature range is desirable.

In some embodiments, the present disclosure provides an apparatus for heat transfer that includes a device and a mechanism for transferring heat to or from the device. The mechanism for transferring heat may include a heat transfer fluid that includes a perfluorinated 1-alkoxypropene of the present disclosure.

In some embodiments, the present disclosure involves: providing an apparatus that includes a heat transfer fluid as described herein; and transferring heat to or from the device using the heat transfer fluid.

The provided apparatus and method for heat transfer may include a device that may be a component, work-piece, assembly, etc. to be cooled, heated or maintained at a predetermined temperature or temperature range. Such devices include electrical components, mechanical components, and optical components. Examples of devices of the present disclosure include, but are not limited to, microprocessors, wafers used to manufacture semiconductor devices, power control semiconductors, electrical distribution switch gear, power transformers, circuit boards, multi-chip modules, packaged and unpackaged semiconductor devices, lasers, fuel cells, and electrochemical cells. In some embodiments, the device can include a chiller, a heater, or a combination thereof.

In certain embodiments, the devices can include electronic devices, such as processors, including microprocessors. As these electronic devices become more powerful, the amount of heat generated per unit time increases. Therefore, the mechanism of heat transfer plays an important role in processor performance. The heat-transfer fluid typically has good heat transfer performance, good electrical compatibility (even if used in "indirect contact" applications such as those employing cold plates), as well as low toxicity, low or nonflammability and low environmental impact. Good electrical compatibility suggests that the heat-transfer fluid candidate exhibit high dielectric strength, high volume resistivity, and poor solvency for polar materials. Additionally, the heat-transfer fluid should exhibit good mechanical compatibility, that is, it should not affect typical materials of construction in an adverse manner.

The mechanism for transferring heat includes one or more perfluorinated 1-alkoxypropene compounds of Formula (I) of the present disclosure. Heat can be transferred by placing the heat transfer mechanism in thermal contact with the device. The heat transfer mechanism, when placed in thermal contact with the device, may remove heat from the device or provide heat to the device, or maintain the device at a selected temperature or temperature range. The direction of heat flow (from device or to device) is determined by the relative temperature difference between the device and the heat transfer mechanism.

The heat transfer mechanism may include facilities for managing the heat-transfer fluid, including, but not limited to, pumps, valves, fluid containment systems, pressure control systems, condensers, heat exchangers, heat sources, heat sinks, refrigeration systems, active temperature control systems, and passive temperature control systems. That is, the mechanism for transferring heat may include a component in a system for maintaining a temperature or temperature range of an electronic device.

Examples of suitable components in heat transfer mechanisms include, but are not limited to, temperature controlled wafer chucks in plasma enhanced chemical vapor deposition (PECVD) tools, temperature-controlled test heads for die performance testing, temperature-controlled work zones within semiconductor process equipment, thermal shock test bath liquid reservoirs, and constant temperature baths. In some systems, such as etchers, ashers, PECVD chambers, and thermal shock testers, the upper desired operating temperature may be as high as 170° C., as high as 200° C., or even as high as 240° C.

The provided apparatus can also include refrigeration systems, cooling systems, testing equipment and machining equipment. In some embodiments, the provided apparatus can be a constant temperature bath or a thermal shock test bath. In some systems, such as etchers, ashers, PECVD chambers, and thermal shock testers, the upper desired operating temperature may be as high as 170° C., as high as 200° C., or even higher.

Immersion Cooling Systems and Methods

Large scale computer server systems can perform significant workloads and generate a large amount of heat during their operation. A significant portion of the heat is generated by the operation of these servers. Due in part to the large amount of heat generated, these servers are typically rack mounted and air-cooled via internal fans and/or fans attached to the back of the rack or elsewhere within the server ecosystem. As the need for access to greater and greater processing and storage resources continues to expand, the density of server systems (i.e., the amount of processing power and/or storage placed on a single server, the number of servers placed in a single rack, and/or the number of servers and/or racks deployed on a single server farm), continue to increase. With the desire for increasing processing or storage density in these server systems, the thermal challenges that result remain a significant obstacle. Conventional cooling systems (e.g., fan based) require large amounts of power, and the cost of power required to drive such systems increases exponentially with the increase in server densities. Consequently, there exists a need for efficient, low power usage system for cooling the servers, while allowing for the desired increased processing and/or storage densities of the server systems.

Thus, in certain embodiments, the apparatus is an immersion cooling system wherein: the mechanism comprises a housing having an interior space and a heat transfer fluid, which is in the form of a liquid, disposed within the interior space; and the device comprises a heat-generating component disposed within the interior space such that the heat-generating component is in contact with the heat transfer fluid (which is a boiling liquid at this stage); wherein the heat transfer fluid comprises a perfluorinated 1-alkoxypropene compound represented by Formula (I).

In some embodiments, the heat-generating component includes an electronic device, such as a computing server. Such computing server may operate at a frequency of greater than 3 GHz.

In some embodiments, the immersion cooling system further includes a heat exchanger disposed within the system such that upon vaporization of the heat transfer fluid liquid to form a heat transfer fluid vapor, the heat transfer fluid vapor contacts the heat exchanger.

In some embodiments, the immersion cooling system includes a two-phase vaporization-condensation immersion cooling system. Two-phase immersion cooling is an emerging cooling technology for the high-performance server computing market that relies on the heat absorbed in the process of vaporizing a liquid (the cooling fluid) to a gas (i.e., the heat of vaporization). The fluids used in this application must meet certain requirements to be viable in the application. For example, the boiling temperature during operation should be in a range of 30° C. to 85° C. Generally, this range accommodates maintaining the server components at a sufficiently cool temperature while allowing heat to be dissipated efficiently to an ultimate heat sink (e.g., outside air). The fluid must be inert so that it is compatible with the materials of construction and the electrical components. Certain perfluorinated and partially fluorinated materials may meet this requirement. The fluid should be stable such that it does not react with common contaminants such as water or with reagents such as activated carbon or alumina that might be used to scrub the fluid during operation. The global warming potential (GWP, 100-yr ITH) and ozone depletion potential (ODP) of the compound should be below acceptable limits, for example, less than 150 and 0, respectively. The fluids should have a dielectric constant (measured at room temperature at 1 KHz) of less than 2.5, such that high frequency electronic components and connectors can be submerged in the fluids without significant loss of signal integrity. Generally, the perfluorinated 1-alkoxypropene compounds of Formula (I) exhibit boiling points (30° C.-85° C.), reactivity, stability, GWPs, and dielectric constants that render them particularly suitable for use as cooling fluids in two-phase immersion cooling systems.

As shown in FIG. 1, in some embodiments, a two-phase immersion cooling system 10 may include a housing 10 having an interior space 15. Within a lower volume 15A of interior space 15, a liquid phase 20 of a heat transfer fluid having an upper liquid surface 20A (i.e., the topmost level of the liquid phase 20) may be disposed. The interior space 15 may also include an upper volume 15B extending from the liquid surface 20A up to an upper portion of the housing 10.

In some embodiments, a heat generating component 25 may be disposed within the interior space 15 such that it is at least partially immersed (and up to fully immersed) in the liquid phase 20 of the heat transfer fluid. That is, while heat generating component 25 is illustrated as being only partially submerged below the upper liquid surface 20A, in some embodiments, the heat generating component 25 may be fully submerged below the liquid surface 20A. In some embodiments, the heat generating components may include one or more electronic devices, such as computing servers.

In various embodiments, a heat exchanger 30 (e.g., a condenser) may be disposed within the upper volume 15B. Generally, the heat exchanger 30 may be configured such that it is able to condense a vapor phase 20B of the heat transfer fluid that is generated as a result of the heat that is produced by the heat generating element 25. For example, the heat exchanger 30 may have an external surface that is maintained at a temperature that is lower than the condensation temperature of a vapor phase of the heat transfer fluid. In this regard, at the heat exchanger 30, a rising vapor phase 20B of the heat transfer fluid may be condensed back to liquid phase or condensate 20C by releasing latent heat to the heat exchanger 30 as the rising vapor phase 20B comes into contact with the heat exchanger 30. The resulting condensate 20C may then be returned back to the liquid phase 20 disposed in the lower volume of 15A.

In some embodiments, immersion cooling systems further include a pump that is configured to move the heat transfer fluid to and from a heat exchanger.

In some embodiments, the immersion cooling system includes a single-phase immersion cooling system. Single-phase immersion cooling has a long history in computer server cooling. There is no phase change in single-phase immersion cooling. Instead the liquid warms and cools as it flows or is pumped to the computer server and a heat exchanger, respectively, thereby transferring heat away from the computer server. The single-phase immersion cooling system is similar to that of the two-phase system in that it may include a heat generating component disposed within the interior space of a housing such that it is at least partially immersed (and up to fully immersed) in the liquid phase of the heat transfer fluid. The single-phase system may further include a pump and a heat exchanger, the pump operating to move the heat transfer fluid to and from the heat generating components and the heat exchanger, and the heat exchanger operating to cool the heat transfer fluid. The heat exchanger may be disposed within or external to the housing.

The fluids used in single-phase immersion cooling of computer servers should meet the same requirements as outlined above with respect to two-phase immersion cooling, except that they typically have higher boiling temperatures to limit evaporative losses. Generally, the perfluorinated 1-alkoxypropene compounds of Formula (I) exhibit boiling points (e.g., 75° C.-200° C.), reactivity, stability, GWPs, and dielectric constants that render them particularly suitable for use as cooling fluids in single-phase immersion cooling systems.

In some embodiments of immersion cooling systems, the perfluorinated 1-alkoxypropene compound is present in the heat transfer fluid within an immersion cooling system in an amount of at least 25 wt-%, at least 50% wt-%, at least 70 wt-%, at least 80 wt-%, at least 90 wt-%, at least 95 wt-%, or at least 99 wt-%, based on the total weight of the heat transfer fluid.

In some embodiments of immersion cooling systems, the heat transfer fluid includes one or more optional components selected from the group of ethers, alkanes, perfluoroalkenes, alkenes, haloalkenes, perfluorocarbons, perfluorinated tertiary amines, perfluoroethers, cycloalkanes, esters, perfluoroketones, ketones, oxiranes, aromatics, siloxanes, hydrochlorocarbons, hydrochlorofluorocarbons, hydrofluorocarbons, hydrofluoroolefins, hydrochloroolefins, hydrochlorofluoroolefins, hydrofluoroethers, or mixtures thereof. In some embodiments, one or more optional components are present in the heat transfer fluid within an immersion cooling system in an amount of up to 75 wt-%, up to 50 wt-%, up to 30 wt-%, up to 20 wt-%, up to 10 wt-%, up to 5 wt-%, or up to 1 wt-%, based on the total weight of the heat transfer fluid.

In some embodiments, the heat transfer fluid within an immersion cooling system has a boiling point of at least 30° C., at least 50° C., or at least 75° C.

In some embodiments, the heat transfer fluid within an immersion cooling system has a boiling point of up to 200° C., up to 85° C., or at least 70° C.

In some embodiments, a method of immersion cooling is provided, wherein the device is a heat generating component. The method includes: at least partially immersing the heat generating component (e.g., a computer server) in the heat transfer fluid, which is in the form of a liquid; and transferring heat from the heat generating component using the heat transfer fluid liquid. In some embodiments of the method, transferring heat from the heat generating component converts the heat transfer fluid liquid to a heat transfer fluid vapor, and the method further includes providing a heat exchanger, and a contacting the heat exchanger with the heat transfer fluid vapor.

While the present disclosure describes examples of suitable two-phase and single-phase immersion cooling systems and methods, it is to be appreciated that the benefits and advantages of the perfluorinated 1-alkoxypropene compounds of Formula (I) may be realized in any known two-phase or single-phase immersion cooling system and method.

Working Fluid

In certain embodiments, the heat transfer fluid is a working fluid. That is, the perfluorinated 1-alkoxypropene compounds of Formula (I) of the present disclosure may be used in an apparatus for converting thermal energy into mechanical energy in a Rankine cycle. The apparatus may further include a heat source to vaporize the working fluid and form a vaporized working fluid, a turbine through which the vaporized working fluid is passed thereby converting thermal energy into mechanical energy, a condenser to cool the vaporized working fluid after it is passed through the turbine, and a pump to recirculate the working fluid.

In some embodiments, the heat is transferred from the heat source to the working fluid in an evaporator or boiler. The vaporized working fluid may be pressurized and can be used to do work by expansion. The heat source can be of any form such as from fossil fuels, e.g., oil, coal, or natural gas. Additionally, in some embodiments, the heat source can come from nuclear power, solar power, or fuel cells. In other embodiments, the heat can be "waste heat" from other heat transfer systems that would otherwise be lost to the atmosphere. The "waste heat," in some embodiments, can be heat that is recovered from a second Rankine cycle system from the condenser or other cooling device in the second Rankine cycle.

An additional source of "waste heat" can be found at landfills where methane gas is flared off. In order to prevent methane gas from entering the environment and thus contributing to global warming, the methane gas generated by the landfills can be burned by way of "flares" producing carbon dioxide and water which are both less harmful to the environment in terms of global warming potential than methane. Other sources of "waste heat" that can be useful in the provided processes are geothermal sources and heat from other types of engines such as gas turbine engines that give off significant heat in their exhaust gases and to cooling liquids such as water and lubricants.

In the provided process, the vaporized working fluid may expand though a device that can convert the pressurized working fluid into mechanical energy. In some embodiments, the vaporized working fluid is expanded through a turbine which can cause a shaft to rotate from the pressure of the vaporized working fluid expanding. The turbine can then be used to do mechanical work such as, in some embodiments, operate a generator, thus generating electricity. In other embodiments, the turbine can be used to drive belts, wheels, gears, or other devices that can transfer mechanical work or energy for use in attached or linked devices.

After the vaporized working fluid has been converted to mechanical energy the vaporized (and now expanded) working fluid can be condensed using a cooling source to liquefy for reuse. The heat released by the condenser can be used for other purposes including being recycled into the same or another Rankine cycle system, thus saving energy. Finally, the condensed working fluid can be pumped by way of a pump back into the boiler or evaporator for reuse in a closed system.

In some embodiments, the perfluorinated 1-alkoxypropene compound is present in the working fluid in an amount of at least 25 wt-%, at least 50% wt-%, at least 70 wt-%, at least 80 wt-%, at least 90 wt-%, at least 95 wt-%, or at least 99 wt-%, based on the total weight of the working fluid.

In some embodiments, the working fluid further includes a co-solvent. In some embodiments, the co-solvent includes alcohols, ethers, alkanes, alkenes, perfluorocarbons, perfluorinated tertiary amines, perfluoroethers, cycloalkanes, esters, ketones, oxiranes, aromatics, siloxanes, hydrochlorocarbons, hydrochlorofluorocarbons, hydrofluorocarbons, hydrofluoroolefins, hydrochlorofluoroolefins, hydrofluoroethers, or mixtures thereof. In some embodiments, the co-solvent is present in the working fluid in an amount of up to 75 wt-%, up to 50 wt-%, up to 30 wt-%, up to 20 wt-%, up to 10 wt-%, up to 5 wt-%, or up to 1 wt-%, based on the total weight of the working fluid.

In some embodiments, the working fluid further includes one or more additives selected from surfactants, coloring agents, stabilizers, anti-oxidants, flame retardants, and mixtures thereof. Minor amounts of such additives can also be added to the working fluids to impart particular desired properties for particular uses.

EMBODIMENTS

Embodiment 1 is an apparatus for heat transfer comprising: a device; and a mechanism for transferring heat to or from the device, the mechanism comprising a heat transfer fluid comprising a perfluorinated 1-alkoxypropene compound represented by the following general Formula (I):

$$R_fO\text{—}CF\text{=}CFCF_3 \qquad \text{I}$$

wherein $R_f$ is a linear, branched, or cyclic perfluoroalkyl group having 2 to 10 carbon atoms and optionally further including 1 to 3 nitrogen and/or 1 to 4 oxygen catenary heteroatoms.

Embodiment 2 is the apparatus of embodiment 1 wherein $R_f$ is a linear, branched, or cyclic perfluoroalkyl group having 2 to 10 carbon atoms and further including 1 to 3 nitrogen and/or 1 to 4 oxygen catenary heteroatoms.

Embodiment 3 is the apparatus of embodiment 2 wherein $R_f$ is a linear, branched, or cyclic perfluoroalkyl group having 2 to 10 carbon atoms and further including a N- and/or O-containing 5- or 6-membered perfluorinated ring.

Embodiment 4 is the apparatus of any one of embodiments 1 to 3 wherein $R_f$ is a linear perfluoroalkyl group.

Embodiment 5 is the apparatus of embodiment 4 wherein $R_f$ is a linear perfluoroalkyl group having 2 to 6 carbon atoms and optionally further including 1 to 3 nitrogen and/or 1 to 4 oxygen catenary heteroatoms.

Embodiment 6 is the apparatus of any one of embodiments 1 to 5 wherein the heat transfer fluid comprises a mixture of perfluorinated 1-alkoxypropene compounds of Formula (I), at least a portion of which includes linear $R_f$ groups and at least a portion of which includes branched $R_f$ groups.

Embodiment 7 is the apparatus of any one of embodiments 1 to 6 wherein the heat transfer fluid comprises a perfluorinated 1-alkoxypropene compound of Formula (I) in a cis configuration.

Embodiment 8 is the apparatus of any one of embodiments 1 to 7 wherein the heat transfer fluid comprises a perfluorinated 1-alkoxypropene compound of Formula (I) in a trans configuration.

Embodiment 9 is the apparatus of any one of embodiments 1 to 8 wherein the heat transfer fluid comprises a mixture of perfluorinated 1-alkoxypropene compounds of Formula (I), at least a portion of which are in the cis configuration and at least a portion of which are in the trans configuration.

Embodiment 10 is the apparatus of any one of embodiments 1 to 9 wherein the heat transfer fluid comprises a perfluorinated 1-alkoxypropene compound of Formula (I) wherein $R_f$ is a perfluoroalkyl group including an oxygen atom.

Embodiment 11 is the apparatus of embodiment 10 wherein the heat transfer fluid comprises a perfluorinated 1-alkoxypropene compound of Formula (I) wherein $R_f$ is a perfluoroalkyl group having the formula —$(CF_2)_n OCF_3$, wherein n=1 to 6.

Embodiment 12 is the apparatus of embodiment 10 wherein the heat transfer fluid comprises $CF_3$—O—$(CF_2)_3$—O—CF=CF—$CF_3$.

Embodiment 13 is the apparatus of any one of embodiments 1 to 9 wherein the heat transfer fluid comprises a perfluorinated 1-alkoxypropene compound of Formula (I) wherein $R_f$ is a perfluoroalkyl group that does not include oxygen or nitrogen atoms.

Embodiment 14 is the apparatus of embodiment 13 wherein the heat transfer fluid comprises a perfluorinated 1-alkoxypropene compound of Formula (I) wherein $R_f$ is a perfluoroalkyl group having the formula —$(CF_2)_n CF_3$, wherein n=1 to 6.

Embodiment 15 is the apparatus of embodiment 14 wherein the heat transfer fluid comprises $CF_3$—$CF_2$—O—CF=CF—$CF_3$.

Embodiment 16 is the apparatus of embodiment 14 wherein the heat transfer fluid comprises $CF_3$—$CF_2$—$CF_2$—O—CF=CF—$CF_3$.

Embodiment 17 is the apparatus of any one of embodiments 1 to 9 wherein the heat transfer fluid comprises a perfluorinated 1-alkoxypropene compound of Formula (I) wherein $R_f$ includes a N- and/or O-containing perfluorinated ring selected from the group of:

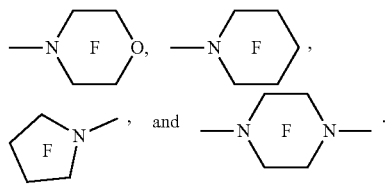

Embodiment 18 is the apparatus of any one of embodiments 1 to 9 wherein the heat transfer fluid comprises a perfluorinated 1-alkoxypropene compound of Formula (I) selected from the group of:

$CF_3CF_2O$—CF=CF—$CF_3$   $CF_3(CF_2)_2O$—CF=CF—$CF_3$   $CF_3(CF_2)_3O$—CF=CF—$CF_3$   $CF_3(CF_2)_4O$—CF=CF—$CF_3$   $CF_3(CF_2)_5O$—CF=CF—$CF_3$   $CF_3(CF_2)_6O$—CF=CF—$CF_3$   $CF_3(CF_2)_7O$—CF=CF—$CF_3$   $CF_3O(CF_2)_3O$—CF=CF—$CF_3$   $CF_3OCF_2OCF_2CF_2O$—CF=CF—$CF_3$   $CF_3OCF_2OCF_2OCF_2CF_2O$—CF=CF—$CF_3$

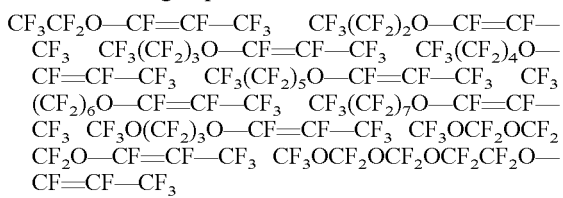

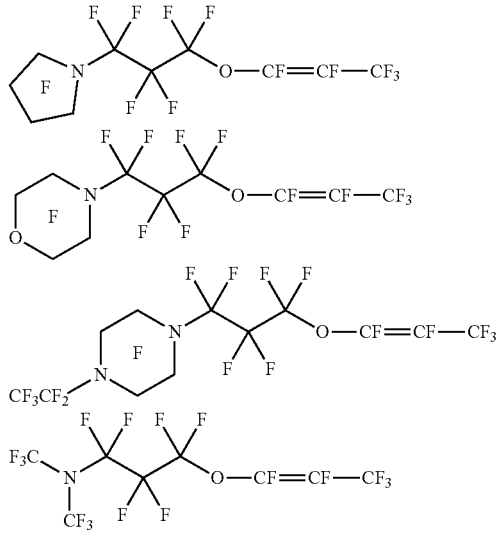

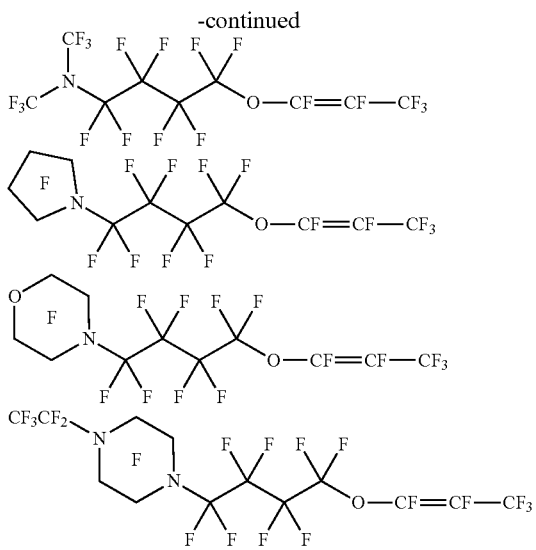

Embodiment 19 is the apparatus of any one of embodiments 1 to 18 wherein the heat transfer fluid comprises a perfluorinated 1-alkoxypropene compound of Formula (I) having a dielectric constant of less than 2.5 (less than 2.4, less than 2.3, less than 2.2, less than 2.1, less than 2.0, or less than 1.9), as measured in accordance with ASTM D150-11 at room temperature and 1 KHz.

Embodiment 20 is the apparatus of any one of embodiments 1 to 19 wherein the heat transfer fluid comprises a perfluorinated 1-alkoxypropene compound of Formula (I) having a global warming potential (GWP) of less than 150 (less than 120, less than 100, less than 80, less than 50, less than 25, or less than 10).

Embodiment 21 is the apparatus of any one of embodiments 1 to 20 wherein the heat transfer fluid comprises a perfluorinated 1-alkoxypropene compound of Formula (I) that is nonflammable.

Embodiment 22 is the apparatus of any one of embodiments 1 to 21 wherein the heat transfer fluid comprises a perfluorinated 1-alkoxypropene compound of Formula (I) having a pour point of less than −100° C. (less than −120° C., less than −130° C., or less than −140° C.).

Embodiment 23 is the apparatus of any one of embodiments 1 to 22 wherein the heat transfer fluid comprises a perfluorinated 1-alkoxypropene compound of Formula (I) having an LD 50 value of at least 5,000 ppm (at least 10,000 ppm, at least 15,000 ppm, or at least 20,000 ppm).

Embodiment 24 is the apparatus of any one of embodiments 1 to 23 wherein the heat transfer fluid comprises a perfluorinated 1-alkoxypropene compound of Formula (I) in purified form.

Embodiment 25 is the apparatus of any one of embodiments 1 to 24 wherein the device is selected from a microprocessor, a semiconductor wafer used to manufacture a semiconductor device, a power control semiconductor, an electrochemical cell, an electrical distribution switch gear, a power transformer, a circuit board, a multi-chip module, a packaged or unpackaged semiconductor device, a fuel cell, and a laser.

Embodiment 26 is the apparatus of any one of embodiments 1 to 25 wherein the mechanism for transferring heat comprises a component in a system for maintaining a temperature or temperature range of an electronic device.

Embodiment 27 is the apparatus of any one of embodiments 1 to 26 which is an immersion cooling system wherein: the mechanism comprises a housing having an interior space and a heat transfer fluid, which is in the form of a liquid, disposed within the interior space; and the device comprises a heat-generating component disposed within the interior space such that the heat-generating component is in contact with the heat transfer fluid (boiling liquid at this stage); wherein the heat transfer fluid comprises a perfluorinated 1-alkoxypropene compound represented by Formula (I).

Embodiment 28 is the apparatus of embodiment 27 wherein the heat-generating component comprises an electronic device.

Embodiment 29 is the apparatus of embodiment 28 wherein the electronic device comprises a computing server.

Embodiment 30 is the apparatus of embodiment 29 wherein the computing server operates at a frequency of greater than 3 GHz.

Embodiment 31 is the apparatus of any one of embodiments 27 to 30 wherein the immersion cooling system further comprises a heat exchanger disposed within the system such that upon vaporization of the heat transfer fluid liquid to form a heat transfer fluid vapor, the heat transfer fluid vapor contacts the heat exchanger.

Embodiment 32 is the apparatus of any one of embodiments 27 to 31 wherein the immersion cooling system comprises a two-phase immersion cooling system.

Embodiment 33 is the apparatus of any one of embodiments 27 to 31 wherein the immersion cooling system comprises a single-phase immersion cooling system.

Embodiment 34 is the apparatus of any one of embodiments 27 to 33 wherein the immersion cooling system further comprises a pump that is configured to move the heat transfer fluid to and from a heat exchanger.

Embodiment 35 is the apparatus of any one of embodiments 27 to 34 wherein the perfluorinated 1-alkoxypropene compound is present in the heat transfer fluid within an immersion cooling system in an amount of at least 25 wt-% (at least 50% wt-%, at least 70 wt-%, at least 80 wt-%, at least 90 wt-%, at least 95 wt-%, or at least 99 wt-%), based on the total weight of the heat transfer fluid.

Embodiment 36 is the apparatus of any one of embodiments 27 to 35 wherein the heat transfer fluid within an immersion cooling system further comprises one or more optional components selected from the group of ethers, alkanes, perfluoroalkenes, alkenes, haloalkenes, perfluorocarbons, perfluorinated tertiary amines, perfluoroethers, cycloalkanes, esters, perfluoroketones, ketones, oxiranes, aromatics, siloxanes, hydrochlorocarbons, hydrochlorofluorocarbons, hydrofluorocarbons, hydrofluoroolefins, hydrochloroolefins, hydrochlorofluoroolefins, hydrofluoroethers, or mixtures thereof.

Embodiment 37 is the apparatus of embodiment 36 wherein the one or more optional components are present in the heat transfer fluid within an immersion cooling system in an amount of up to 75 wt-% (up to 50 wt-%, up to 30 wt-%, up to 20 wt-%, up to 10 wt-%, up to 5 wt-%, or up to 1 wt-%), based on the total weight of the heat transfer fluid.

Embodiment 38 is the apparatus of any one of embodiments 27 to 37 wherein the heat transfer fluid within an immersion cooling system has a boiling point of 30° C.-200° C. (30° C.-85° C., 50° C.-70° C., or 75° C.-200° C.).

Embodiment 39 is the apparatus for heat transfer of any one of embodiments 1 to 24 wherein the heat transfer fluid is a working fluid.

Embodiment 40 is the apparatus of embodiment 39 wherein the perfluorinated 1-alkoxypropene compound is present in the working fluid in an amount of at least 25 wt-% (at least 50% wt-%, at least 70 wt-%, at least 80 wt-%, at least 90 wt-%, at least 95 wt-%, or at least 99 wt-%), based on the total weight of the working fluid.

Embodiment 41 is the apparatus of embodiment 39 or 40 wherein the working fluid further comprises a co-solvent.

Embodiment 42 is the apparatus of embodiment 41 wherein the co-solvent comprises alcohols, ethers, alkanes, alkenes, perfluorocarbons, perfluorinated tertiary amines, perfluoroethers, cycloalkanes, esters, ketones, oxiranes, aromatics, siloxanes, hydrochlorocarbons, hydrochlorofluorocarbons, hydrofluorocarbons, hydrofluoroolefins, hydrochlorofluoroolefins, hydrofluoroethers, or mixtures thereof.

Embodiment 43 is the apparatus of embodiment 41 or 42 wherein the co-solvent is present in the working fluid in an amount of up to 75 wt-% (up to 50 wt-%, up to 30 wt-%, up to 20 wt-%, up to 10 wt-%, up to 5 wt-%, or up to 1 wt-%), based on the total weight of the working fluid.

Embodiment 44 is the apparatus of any one of embodiments 39 to 43 wherein the working fluid further comprises one or more additives selected from surfactants, coloring agents, stabilizers, anti-oxidants, flame retardants, and mixtures thereof.

Embodiment 45 is a method of transferring heat comprising: providing an apparatus comprising a heat transfer fluid of any one of embodiments 1 to 44; providing a device; and transferring heat to or from the device using the heat transfer fluid.

Embodiment 46 is a method of transferring heat comprising: providing a device; and transferring heat to or from the device using a heat transfer fluid comprising a perfluorinated 1-alkoxypropene compound represented by the following general Formula (I):

$$R_fO—CF=CFCF_3 \quad\quad I$$

wherein $R_f$ is a linear, branched, or cyclic perfluoroalkyl group having 2 to 10 carbon atoms and optionally further including 1 to 3 nitrogen and/or 1 to 4 oxygen catenary heteroatoms.

Embodiment 47 is the method of embodiment 46 which is a method of immersion cooling, wherein the device is a heat generating component, the method comprising: at least partially immersing the heat generating component (e.g., a computer server) in the heat transfer fluid, which is in the form of a liquid; and transferring heat from the heat generating component using the heat transfer fluid liquid.

Embodiment 48 is the method of embodiment 47 wherein transferring heat from the heat generating component converts the heat transfer fluid liquid to a heat transfer fluid vapor, and the method further includes providing a heat exchanger, and a contacting the heat exchanger with the heat transfer fluid vapor.

Embodiment 49 is a perfluorinated 1-alkoxypropene compound represented by the following general Formula (I):

$$R_fO—CF=CFCF_3 \quad\quad I$$

wherein $R_f$ is a linear, branched, or cyclic perfluoroalkyl group having 2 to 10 carbon atoms (preferably 3 to 10 carbon atoms) and optionally further including 1 to 3 nitrogen and/or 1 to 4 oxygen catenary heteroatoms; with the proviso that $R_f$ is not a branched perfluoroalkyl group having 3 carbon atoms and no heteroatoms.

Embodiment 50 is the compound of embodiment 49 with the proviso that $R_f$ is not a branched perfluoroalkyl group having no heteroatoms.

Embodiment 51 is the compound of embodiment 50 wherein $R_f$ is a linear, branched, or cyclic perfluoroalkyl group having 2 to 10 carbon atoms and further including 1 to 3 nitrogen and/or 1 to 4 oxygen catenary heteroatoms.

Embodiment 52 is the compound of embodiment 51 wherein $R_f$ is a linear, branched, or cyclic perfluoroalkyl group having 2 to 10 carbon atoms and further including a N- and/or O-containing 5- or 6-membered perfluorinated ring.

Embodiment 53 is the compound of embodiment 49 wherein $R_f$ is a linear perfluoroalkyl group.

Embodiment 54 is the compound of embodiment 53 wherein $R_f$ is a linear perfluoroalkyl group having 2 to 6 carbon atoms and optionally further including 1 to 3 nitrogen and/or 1 to 4 oxygen catenary heteroatoms.

Embodiment 55 is the compound of any one of embodiments 49 to 54 in a cis configuration.

Embodiment 56 is the compound of any one of embodiments 49 to 54 in a trans configuration.

Embodiment 57 is the compound of any one of embodiments 49 to 56 wherein $R_f$ is a perfluoroalkyl group including an oxygen atom.

Embodiment 58 is the compound of embodiment 57 wherein $R_f$ is a perfluoroalkyl group having the formula $—(CF_2)_nOCF_3$, wherein n=1 to 6.

Embodiment 59 is the compound of embodiment 58 which is $CF_3—O—(CF_2)_3—O—CF=CF—CF_3$.

Embodiment 60 is the compound of any one of embodiments 49 to 56 wherein $R_f$ is a perfluoroalkyl group that does not include oxygen or nitrogen atoms.

Embodiment 61 is the compound of embodiment 60 wherein $R_f$ is a perfluoroalkyl group having the formula $—(CF_2)_nCF_3$, wherein n=1 to 6.

Embodiment 62 is the compound of embodiment 61 which is $CF_3—CF_2—O—CF=CF—CF_3$.

Embodiment 63 is the compound of embodiment 61 which is $CF_3—CF_2—CF_2—O—CF=CF—CF_3$.

Embodiment 64 is the compound of any one of embodiments 49 to 56 wherein $R_f$ includes a N- and/or O-containing perfluorinated ring selected from the group of:

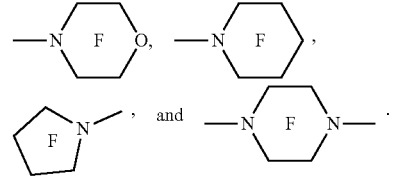

Embodiment 65 is the compound of any one of embodiments 49 to 56 selected from the group of:
$CF_3CF_2O—CF=CF—CF_3$  $CF_3(CF_2)_2O—CF=CF—CF_3$  $CF_3(CF_2)_3O—CF=CF—CF_3$  $CF_3(CF_2)_4O—CF=CF—CF_3$  $CF_3(CF_2)_5O—CF=CF—CF_3$  $CF_3(CF_2)_6O—CF=CF—CF_3$  $CF_3(CF_2)_7O—CF=CF—CF_3$  $CF_3O(CF_2)_3O—CF=CF—CF_3$  $CF_3OCF_2OCF_2CF_2O—CF=CF—CF_3$  $CF_3OCF_2OCF_2OCF_2CF_2O—CF=CF—CF_3$

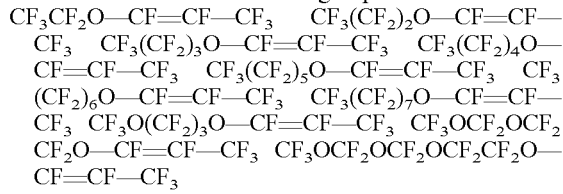

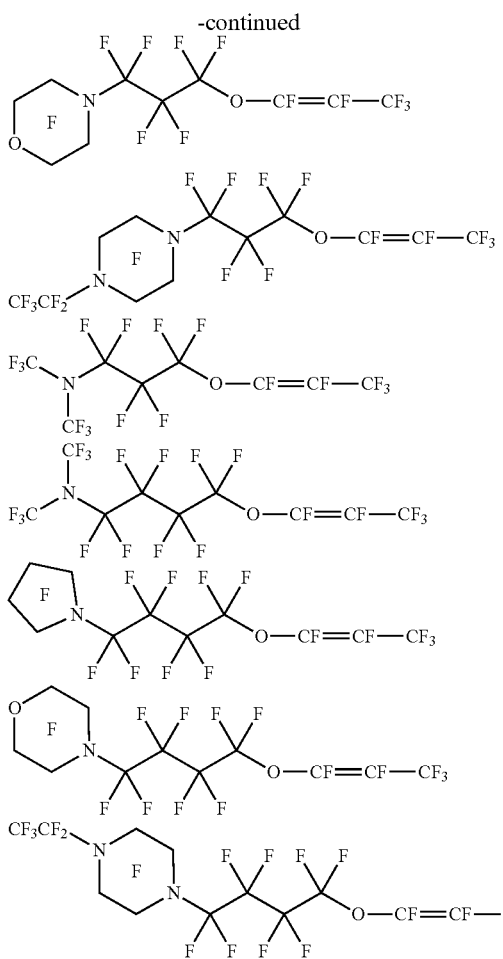

Embodiment 66 is the compound of any one of embodiments 49 to 65 having a dielectric constant of less than 2.5 (less than 2.4, less than 2.3, less than 2.2, less than 2.1, less than 2.0, or less than 1.9), as measured in accordance with ASTM D150-11 at room temperature and 1 KHz.

Embodiment 67 is the compound of any one of embodiments 49 to 66 having a global warming potential (GWP) of less than 150 (less than 120, less than 100, less than 80, less than 50, less than 25, or less than 10).

Embodiment 68 is the compound of any one of embodiments 49 to 67 which is nonflammable.

Embodiment 69 is the compound of any one of embodiments 49 to 68 having a pour point of less than −100° C. (less than −120° C., less than −130° C., or less than −140° C.).

Embodiment 70 is the compound of any one of embodiments 49 to 69 having an LD 50 value of at least 5,000 ppm (at least 10,000 ppm, at least 15,000 ppm, or at least 20,000 ppm).

EXAMPLES

Unless otherwise noted, all parts, percentages, ratios, etc. in the examples and the rest of the specification are by weight, and all reagents used in the examples were obtained, or are available, from general chemical suppliers such as, for example, Sigma-Aldrich, Saint Louis, Mo., or may be synthesized by conventional methods. The following abbreviations are used in this section: mL=milliliter, sec=seconds, min=minutes, h=hours, g=gram, mmol=millimole, ° C.=degrees Celsius, cSt=centistokes, mmHg=millimeters mercury, kPa=kiloPascal, GC-FID=gas chromatography-flame ionization detection, NMR=nuclear magnetic resonance, W=watts, V=volts, kV=kilovolts, cm=centimeters, mm=millimeters, μm=micrometers, kHz=kilohertz.

TABLE 1

Materials

| Material | Description |
| --- | --- |
| KF | Potassium fluoride, commercially available from Sigma-Aldrich Corp. |
| CsF | Cesium fluoride, commercially available from Alfa Aesar, Ward Hill, MA, USA |
| SbF$_5$ | Antimony(V) pentafluoride, commercially available from SynQuest Laboratories |
| Diglyme | Diethylene glycol dimethyl ether, commercially available from Sigma-Aldrich Corp. |
| AlCl$_3$ | Aluminum(III) chloride, commercially available from Sigma-Aldrich Corp. |
| Activated carbon | Commercially available from Alfa Aesar |
| K$_2$CO$_3$ | Potassium carbonate, commercially available from Alfa Aesar |
| 4 angstrom molecular sieves | Commercially available from Sigma-Aldrich Corp. |
| SiO$_2$ | Silica gel, commercially available from Sigma-Aldrich Corp. |
| Basic alumina | Commercially available from Alfa Aesar |
| Celite | Commercially available from Sigma-Aldrich Corp. |
| MA-3 | 1,1,2,3,3 -Pentafluoro-3-(perfluoropropoxy)prop-1-ene, commercially available from Anles, Ltd., St. Petersburg, Russia |
| MA-31 | 1,1,2,3,3-Pentafluoro-3-(1,1,2,2,3,3-hexafluoro-3-(trifluoromethoxy)propoxy)prop-l-ene, commercially available from Anles, Ltd. |
| FC-72 | Engineered fluid available under the trade designation "3M FLUORINERT ELECTRONIC LIQUID FC-72" from 3M Company, Maplewood, MN, USA |
| FC-77 | Engineered fluid available under the trade designation "3M FLUORINERT ELECTRONIC LIQUID FC-77" from 3M Company |

Preparatory Example 1 (PE-1): Selective Preparation of 1,2,3,3,3-pentafluoro-1-(perfluoropropoxy)prop-1-ene (MP-3) Via SbF$_5$-Catalyzed Isomerization of 1,1,2,3,3-pentafluoro-3-(perfluoropropoxy)prop-1-ene (MA-3)

MA-3 (50 g, 160 mmol) was charged to a 3-neck flask equipped with a water-cooled condenser and magnetic stir bar. SbF$_5$ was then added dropwise to the stirring MA-3 and a large exotherm was observed. The resultant reaction mixture was allowed to stir at room temperature for 1 h. GC-FID analysis of the reaction mixture indicated complete consumption of the MA-3 starting material. Water was then added to the mixture with stirring. The fluorous phase was collected and distilled by concentric tube distillation (59° C., 740 mmHg, 98.7 kPa) affording the desired MP-3 (41.2 g, 82% yield) as a colorless liquid. Both E- and Z-isomers were obtained as a mixture. A toxicity screening study in rats indicated that the 4 h inhalation LC-50 of MP-3 is greater than 10,000 ppm. The structure was confirmed by GC-MS and $^{19}$F NMR analyses to be that of the desired product.

Preparatory Example 2 (PE-2): Selective Preparation of 1,2,3,3,3-pentafluoro-1-(1,1,2,2,3,3-hexafluoro-3-(trifluoromethoxy)propoxy)prop-1-ene (MP-31) Via AlCl$_3$-Catalyzed Isomerization of 1,1,2,3,3-Pentafluoro-3-(1,1,2,2,3,3-hexafluoro-3-(trifluoromethoxy)propoxy)prop-1-ene (MA-31)

A 500-mL round-bottom flask charged with AlCl$_3$ (4.2 g, 31 mmol) and equipped with a magnetic stir bar and an addition funnel was evacuated under reduced pressure and back-filled with nitrogen gas three times. The addition funnel was then charged with MA-31 (201 g, 526 mmol), which was then added dropwise to the stirring AlCl$_3$ over the course of one hour. No rise in temperature was observed. The resultant reaction mixture was allowed to stir overnight at room temperature and was then filtered over a pad of celite. The collected colorless liquid was purified via fractional distillation with a concentric tube column (91° C., 740 mmHg, 98.7 kPa) affording MP-31 (170 g, 85% yield) as a colorless liquid. Both E- and Z-isomers were obtained as a mixture. The structure was confirmed by GC-MS and $^{19}$F NMR analyses to be that of the desired product.

Comparative Preparatory Example 1 (CPE-1): Disproportionation of 1,1,2,3,3-pentafluoro-3-(1,1,2,2,3,3-hexafluoro-3-(trifluoromethoxy)propoxy)prop-1-ene (MA-31) by CsF To a 300-mL Hastelloy reactor equipped with an overhead stirrer were added diglyme (53 mL), CsF (5.0 g, 33 mmol), and MA-31 (50 g, 131 mmol). Stirring commenced and the reaction mixture was slowly raised to 50° C. followed by an overnight stir. To the resultant mixture was then added H$_2$O (100 mL) and the bottom fluorous layer was collected and analyzed by GC-FID analysis which revealed no formation of MP-31 and complete conversion of the MA-31 starting material. GC-MS analysis of the crude fluorous material revealed that 69% of the mixture (uncorrected GC yield of 57%) was a ketone possessing the same molecular weight as MA-31 and MP-31. Fractional distillation of the fluorous layer with a concentric tube column (78-79° C., 740 mmHg, 98.7 kPa) afforded 1,1,1,2,4,4,5,5-octafluoro-5-(trifluoromethoxy)-2-(trifluoromethyl)pentan-3-one (20 g). The structure was confirmed by GC-MS and $^{19}$F NMR analyses to be that of disproportionation ketone product 1,1,1,2,4,4,5,5-octafluoro-5-(trifluoromethoxy)-2-(trifluoromethyl)pentan-3-one. This method demonstrates the use of a common metal fluoride salt, which results in disproportionation leading to nearly exclusive formation of a perfluorinated ketone.

Example 1 (EX-1): Viscosity and Pour Point of PE-1 and PE-2

Kinematic Viscosity of PE-1 and PE-2 was measured using Schott-Ubbelohde Viscometers (glass capillary viscometers). The viscometers were timed using a viscometer timer available under the trade designation AVS-350 from SI Analytics, College Station, Tex., USA. The viscometer measurement stand and glass viscometer were immersed in a temperature-controlled liquid bath filled with an engineered fluid available under the trade designation "3M NOVEC 7500 ENGINEERED FLUID" available from 3M Company, Maplewood, Minn., USA. The temperature-controlled liquid bath available from Lawler Manufacturing Corporation, Edison, N.J., USA, was fitted with a copper tubing coil for liquid nitrogen cooling with fine temperature control provided by the bath's electronic temperature control heater. The fluid was mechanically stirred to provide uniform temperature in the bath. The bath controlled temperature within ±0.1° C., measured by the built-in RTD temperature sensor. The sample liquid was added to the viscometer between the two fill lines etched on the viscometer. The viscometer timer automatically pumped the sample fluid above the upper timing mark, then released the fluid and measured the efflux times between the upper and lower timing marks. The fluid meniscus was detected by optical sensors as it passed each timing mark. The sample was drawn up and measured repeatedly; the results in Table 2 below are the averages of multiple determinations. The glass viscometers were calibrated using certified kinematic viscosity standard fluids available from Cannon Instrument Company, State College, Pa., USA, to obtain a calibration constant (cSt/sec) for each viscometer.

The measured Kinematic Viscosity in centistokes, which is the average efflux time (sec)×constant (cSt/sec), for each of PE-1 and PE-2 is shown in Table 2. This data indicates that PE-1 and PE-2 are suitable for use as heat transfer fluids.

TABLE 2

Kinematic Viscosity of PE-1 and PE-2

| Temp ° C. | Kinematic Viscosity, cSt (m$^2$/s) | |
| --- | --- | --- |
| | PE-1 | PE-2 |
| 0.0 | 0.38 (3.8e$^{-7}$) | 0.70 (7e$^{-7}$) |
| −10.0 | 0.44 (4.4e$^{-7}$) | 0.83 (8.3e$^{-7}$) |
| −20.0 | 0.58 (5.8e$^{-7}$) | 1.00 (1e$^{-6}$) |
| −40.0 | 0.85 (8.5e$^{-7}$) | 1.38 (1.38e$^{-6}$) |
| −50.0 | 1.07 (1.07e$^{-6}$) | 1.83 (1.83e$^{-6}$) |
| −60.0 | 1.40 (1.4e$^{-6}$) | 2.56 (2.56e$^{-6}$) |

Pour point of PE-2 was determined visually and defined as the lowest temperature at which the sample was observed to flow within 5 sec while being held horizontally. One to two milliliters of the sample were placed in a vial and cooled in a bath until it solidified. The sample was then allowed to warm slowly in the bath and observed every 3-5° C.

TABLE 3

Pour point (° C.) of PE-1 and PE-2
Pour point (° C.) of PE-1 and PE-2

| PE-1 | PE-2 |
| --- | --- |
| −145 | −140 |

Example 2 (EX-2): Vapor Pressure and Boiling Point of PE-1 and PE-2

Vapor Pressure was measured using the stirred-flask ebulliometer method described in ASTM E1719-97 "Vapor Pressure Measurement by Ebulliometry." This method is also referred to as "Dynamic Reflux." The boiling point was measured using ASTM D1120-94 "Standard Test Method for Boiling Point of Engine Coolants." The method used a 50-mL glass round-bottom flask. Vacuum was measured and controlled using a vacuum controller available from J-KEM Scientific, Inc., St. Louis, Mo., USA. The pressure transducer was calibrated on the day of measurement by comparison with full vacuum and with an electronic barometer located in the same laboratory. The procedure was carried out by slowly heating the material, then applying vacuum until boiling occurred and a steady dropwise reflux rate was established. Pot temperature and pressure reading were recorded, then the vacuum controller was set for a higher absolute pressure and the material was heated further until a new reflux point was established. The pressure level was raised in increments until the vapor pressure curve was obtained up to the atmospheric boiling point.

The vapor pressures of PE-1 at various temperatures are shown in Table 4 below. The boiling point of PE-1 is 60.1° C., which is the temperature at 760 mmHg. The vapor pressures of PE-2 at various temperatures are shown in Table 5 below. The boiling point of PE-2 is 88.1° C., which is the temperature at 760 mmHg.

TABLE 4

Vapor Pressure Results for PE-1

| Temp (° C.) | Vapor Pressure, mmHg (kPa) |
|---|---|
| 31.2 | 243.1 (32.4) |
| 39.2 | 344.1 (45.9) |
| 45.4 | 440.0 (58.7) |
| 53.4 | 593.1 (79.1) |
| 59.7 | 737.4 (98.3) |
| 60.1 | 760 (101.3) |

TABLE 5

Vapor Pressure Results for PE-2

| Temp (° C.) | Vapor Pressure, mmHg (kPa) |
|---|---|
| 24.1 | 49.5 (6.6) |
| 37.2 | 99.4 (13.3) |
| 52.4 | 196.4 (26.1) |
| 69.3 | 394.4 (52.6) |
| 87.2 | 736.8 (98.2) |
| 88.1 | 760 (101.3) |

Example 3 (EX-3): Thermal Stability Data for PE-2

The thermal stability was measured by charging 1.0 g of Preparatory Example 2 into glass vials and then adding 0.10 g of absorbent. The samples were stirred for 24 h at 50° C. and then analyzed by GC-FID for decomposition and purity changes. The thermal stability testing results with various absorbents are shown in Table 6 below. This data demonstrates PE-2 has sufficient thermal stability to be a suitable heat transfer material.

TABLE 6

Thermal Stability Results

| | No Absorbent | Activated Carbon | 4 Angstrom Molecular Sieves | $K_2CO_3$ | Basic Alumina | Silica Gel |
|---|---|---|---|---|---|---|
| Purity (%) | 99.5 | 99.5 | 99.5 | 99.3 | 99.5 | 99.4 |

Examples 4 and 5 (EX-4 and EX-5) and Counter Examples 1-4 (CE-1, CE-2, CE-3, and CE-4)

Dielectric breakdown strength and dielectric constant were measured for PE-1, PE-2, CE-1 to CE-4. The dielectric constants presented in Table 7, below, were measured using the broadband Novocontrol Dielectric Spectrometer per ASTM D150-11. The dielectric breakdown strengths presented in Table 7 were measured according to ASTM D877-13, Procedure A, with the following modification: spacing between the electrodes was 2.54 mm and rate of rise was 500 V/sec.

This data demonstrates the stability of PE-1 and PE-2 in high voltage applications and the advantage of the position of the double bond (compare EX-5 to CE-1 and EX-6 to CE-2). Also, PE-1 and PE-2 demonstrate dielectric breakdown voltages as good as or better than commonly used heat transfer fluids FC-72 and FC-77.

TABLE 7

Dielectric Breakdown Voltage and Dielectric Constant Results

| Example or Counter Example | Material | Dielectric Breakdown Voltage (kV) | Dielectric Constant (measured at 1 kHz) |
|---|---|---|---|
| EX-5 | PE-1 | 41.7 | 2.04 |
| EX-6 | PE-2 | >60 | 2.04 |
| CE-1 | MA-3 | 30.7 | 2.37 |
| CE-2 | MA-31 | 39.4 | 2.37 |
| CE-3 | FC-72 | 38 | 1.76 |
| CE-4 | FC-77 | 40 | 1.86 |

Example 6 (EX-6) and Counter Example 5 (CE-5): Measurement of Heat Transfer Coefficients of PE-1 and FC-72

The heat transfer apparatus used for the measurement of change in heat transfer coefficient (HTC) as a function of heat flux is described below. The test apparatus comprised a phenolic platform containing a 25-mm diameter copper heater atop 4 thin radial ribs. A thermocouple probe integrated into the platform above the heater was placed so that a greased boiling enhancement coating (BEC) disk could be placed onto the probe and atop the heater. The BEC, obtained from Celsia, Santa Clara, Calif., USA with an identification number of 01MMM02-A1, had a thickness of 300 μm, was comprised of 50 μm particles, and was coated in a 5 cm² area on a 3-mm thick, 100 series copper disk. The thermocouple probe was bent in such a way that when the disk was locked down into the proper x-y position, the probe was gently pressed upward and into the termination of the thermocouple groove to measure the sink temperature ($T_s$). The platform moved on z-axis sliders with a lever and spring that engaged the BEC disk to a gasketed glass tube into which another thermocouple protruded to measure $T_f$, the fluid saturation temperature.

Approximately 10 mL of fluid was added through a fill port at the top of the apparatus. Vapor was condensed in an air-cooled condenser and fell back to the pool. The condenser was open at the top so that $P=P_{atm}$ and $Tf=Tb=T_s$ ($P_{atm}$).

Measurements began with a 3-min warm-up at 100 W (20 W/cm²) intended to minimize conduction losses from the bottom of the copper heater during subsequent measurements. The power was then lowered to 50 W (10 W/cm$^2$) and allowed to equilibrate for 2 min at which time data were recorded before advancing 10 W to the next data point. This continued until $T_s$ exceeded a preset limit, usually about Tb+20° C. The data acquisition system queried the DC power supply for the heater voltage, V, and current, I. The heat flux, Q", and heat transfer coefficient, H, are defined as Q"=Q/A=VI/A and H=Q"/($T_s$-$T_f$), where A is area. Heat transfer measurement results are presented in Table 8, below.

This data demonstrates PE-1 has superior heat transfer characteristics compared to commonly used heat transfer fluid FC-72.

TABLE 8

Heat Transfer Coefficients of PE-1 and FC-72

| Heat flux (Q" (W/cm$^2$)) | Heat transfer coefficient (H (W/cm$^2$-K)) | |
|---|---|---|
| | CE-5 (FC-72) | EX-6 (PE-1) |
| 12.8 | 5.86 | 6.98 |
| 15.3 | 5.86 | 7.11 |
| 17.8 | 5.94 | 7.16 |
| 20.4 | 6.23 | 7.41 |
| 22.6 | 6.47 | 7.67 |
| 25.0 | 6.71 | 7.91 |
| 27.5 | 6.91 | 8.08 |
| 29.8 | 7.16 | 8.20 |
| 32.2 | 7.32 | 8.29 |
| 34.6 | 7.66 | 8.53 |
| 37.0 | 7.81 | 8.68 |
| 39.3 | 7.40 | 8.57 |

Example 7 (EX-7): Measurement of Atmospheric Lifetime and Global Warming Potential (GWP) Values of PE-2

A measured IR cross-section was used to calculate the radiative forcing value for PE-2 using the method of Pinnock et al. (*J. Geophys. Res.* 1995, 100, 23227-23238). Using this radiative forcing value and the experimentally determined atmospheric lifetime (0.16 year), the GWP (100-year iterative time horizon (ITH)) for PE-2 was found to be 3.2. This is less than the GWP of closely related perfluorocarbons. The shorter atmospheric lifetime of PE-2 leads to a lower GWP than related perfluorocarbons.

The complete disclosures of the patents, patent documents, and publications cited herein are incorporated by reference in their entirety as if each were individually incorporated. To the extent that there is any conflict or discrepancy between this specification as written and the disclosure in any document that is incorporated by reference herein, this specification as written will control. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. An apparatus for heat transfer comprising:
   a device; and
   a mechanism for transferring heat to or from the device, the mechanism comprising a heat transfer fluid comprising a perfluorinated 1-alkoxypropene compound represented by the following general Formula (I):

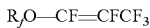

wherein $R_f$ is a linear, branched, or cyclic perfluoroalkyl group having 2 to 10 carbon atoms and optionally further including 1 to 3 nitrogen and/or 1 to 4 oxygen catenary heteroatoms; with the proviso that $R_f$ is not a branched perfluoroalkyl group having 3 carbon atoms and no heteroatoms.

2. The apparatus of claim 1 wherein the heat transfer fluid comprises a mixture of perfluorinated 1-alkoxypropene compounds of Formula (I), at least a portion of which includes linear $R_f$ groups and at least a portion of which includes branched $R_f$ groups.

3. The apparatus of claim 1 wherein the heat transfer fluid comprises a perfluorinated 1-alkoxypropene compound of Formula (I) selected from the group of:
$CF_3CF_2O$—$CF$=$CF$—$CF_3$   $CF_3(CF_2)_2O$—$CF$=$CF$—$CF_3$   $CF_3(CF_2)_3O$—$CF$=$CF$—$CF_3$   $CF_3(CF_2)_4O$—$CF$=$CF$—$CF_3$   $CF_3(CF_2)_5O$—$CF$=$CF$—$CF_3$   $CF_3(CF_2)_6O$—$CF$=$CF$—$CF_3$   $CF_3(CF_2)_7O$—$CF$=$CF$—$CF_3$   $CF_3O(CF_2)_3O$—$CF$=$CF$—$CF_3$   $CF_3OCF_2OCF_2CF_2O$—$CF$=$CF$—$CF_3$   $CF_3OCF_2OCF_2OCF_2CF_2O$—$CF$=$CF$—$CF_3$

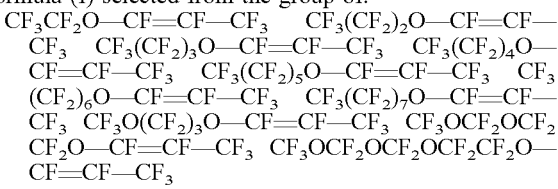

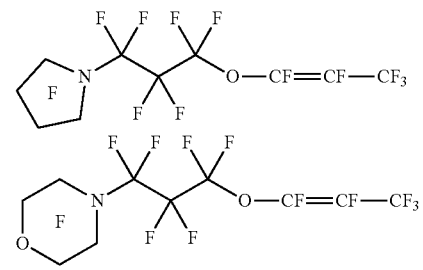

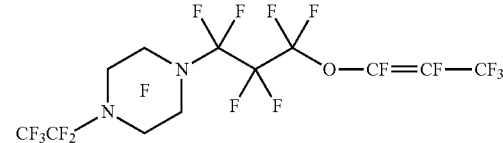

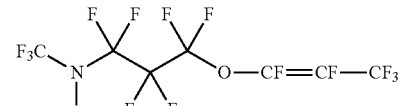

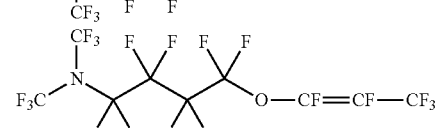

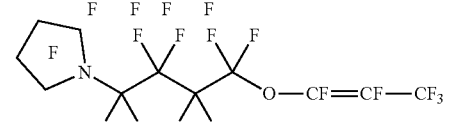

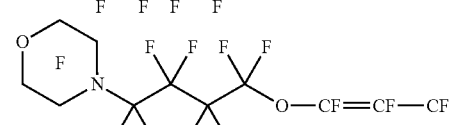

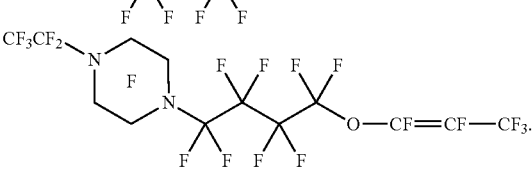

4. The apparatus of claim 1 wherein the heat transfer fluid comprises a perfluorinated 1-alkoxypropene compound of Formula (I) having a dielectric constant of less than 2.5, as measured in accordance with ASTM D150-11 at room temperature and 1 KHz.

5. The apparatus of claim 1 wherein the heat transfer fluid comprises a perfluorinated 1-alkoxypropene compound of Formula (I) having a global warming potential (GWP) of less than 150.

6. The apparatus of claim 1 wherein the heat transfer fluid comprises a perfluorinated 1-alkoxypropene compound of Formula (I) that is nonflammable.

7. The apparatus of claim 1 wherein the heat transfer fluid comprises a perfluorinated 1-alkoxypropene compound of Formula (I) having a pour point of less than −100° C.

8. The apparatus of claim 1 wherein the heat transfer fluid comprises a perfluorinated 1-alkoxypropene compound of Formula (I) having an LD 50 value of at least 5,000 ppm.

9. The apparatus of claim 1 wherein the heat transfer fluid comprises a perfluorinated 1-alkoxypropene compound of Formula (I) in purified form.

10. The apparatus of claim 1 wherein the device is selected from a microprocessor, a semiconductor wafer used to manufacture a semiconductor device, a power control semiconductor, an electrochemical cell, an electrical distribution switch gear, a power transformer, a circuit board, a multi-chip module, a packaged or unpackaged semiconductor device, a fuel cell, and a laser.

11. The apparatus of claim 1 which is an immersion cooling system wherein:
   the mechanism comprises a housing having an interior space and a heat transfer fluid, which is in the form of a liquid, disposed within the interior space; and
   the device comprises a heat-generating component disposed within the interior space such that the heat-generating component is in contact with the heat transfer fluid; wherein the heat transfer fluid comprises a perfluorinated 1-alkoxypropene compound represented by Formula (I).

12. The apparatus for heat transfer of claim 1 wherein the heat transfer fluid is a working fluid.

13. A method of transferring heat comprising:
   providing the apparatus for heat transfer fluid of claim 1; and
   transferring heat to or from the apparatus using the heat transfer fluid.

14. A method of transferring heat comprising:
   providing a device; and
   transferring heat to or from the device using a heat transfer fluid comprising a perfluorinated 1-alkoxypropene compound represented by the following general Formula (I):

$$R_fO\!-\!CF\!=\!CFCF_3 \qquad I$$

wherein $R_f$ is a linear, branched, or cyclic perfluoroalkyl group having 2 to 10 carbon atoms and optionally further including 1 to 3 nitrogen and/or 1 to 4 oxygen catenary heteroatoms; with the proviso that $R_f$ is not a branched perfluoroalkyl group having 3 carbon atoms and no heteroatoms.

15. The method of claim 14 which is a method of immersion cooling, wherein the device is a heat generating component, the method comprising:
   at least partially immersing the heat generating component in the heat transfer fluid, which is in the form of a liquid; and
   transferring heat from the heat generating component using the heat transfer fluid liquid.

16. The method of claim 15 wherein transferring heat from the heat generating component converts the heat transfer fluid liquid to a heat transfer fluid vapor, and the method further includes providing a heat exchanger, and a contacting the heat exchanger with the heat transfer fluid vapor.

17. A perfluorinated 1-alkoxypropene compound represented by the following general Formula (I):

$$R_fO\!-\!CF\!=\!CFCF_3 \qquad I$$

wherein $R_f$ is a linear, branched, or cyclic perfluoroalkyl group having 2 to 10 carbon atoms and optionally further including 1 to 3 nitrogen and/or 1 to 4 oxygen catenary heteroatoms; with the proviso that $R_f$ is not a branched perfluoroalkyl group having 3 carbon atoms and no heteroatoms.

18. The compound of claim 17 selected from the group of:
$CF_3CF_2O\!-\!CF\!=\!CF\!-\!CF_3$ $\quad$ $CF_3(CF_2)_2O\!-\!CF\!=\!CF\!-\!CF_3$ $\quad$ $CF_3(CF_2)_3O\!-\!CF\!=\!CF\!-\!CF_3$ $\quad$ $CF_3(CF_2)_4O\!-\!CF\!=\!CF\!-\!CF_3$ $\quad$ $CF_3(CF_2)_5O\!-\!CF\!=\!CF\!-\!CF_3$ $\quad$ $CF_3(CF_2)_6O\!-\!CF\!=\!CF\!-\!CF_3$ $\quad$ $CF_3(CF_2)_7O\!-\!CF\!=\!CF\!-\!CF_3$ $\quad$ $CF_3O(CF_2)_3O\!-\!CF\!=\!CF\!-\!CF_3$ $\quad$ $CF_3OCF_2OCF_2CF_2O\!-\!CF\!=\!CF\!-\!CF_3$ $\quad$ $CF_3OCF_2OCF_2OCF_2CF_2O\!-\!CF\!=\!CF\!-\!CF_3$

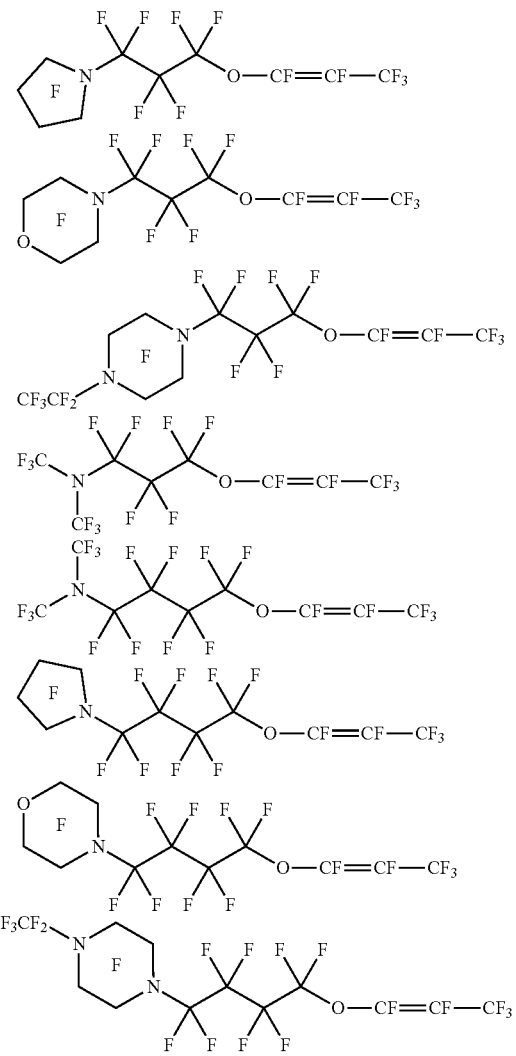

19. The compound of claim 18 which is $CF_3-O-(CF_2)_3-O-CF=CF-CF_3$, $CF_3-CF_2-O-CF=CF-CF_3$, or $CF_3-CF_2-CF_2-O-CF=CF-CF_3$.

20. The compound of claim 17 having a dielectric constant of less than 2.5, as measured in accordance with ASTM D150-11 at room temperature and 1 KHz.

\* \* \* \* \*